United States Patent
Sikora et al.

(10) Patent No.: US 11,008,616 B2
(45) Date of Patent: May 18, 2021

(54) CORRECTING FOR DEAMINATION-INDUCED SEQUENCE ERRORS

(71) Applicant: GUARDANT HEALTH, INC., Redwood City, CA (US)

(72) Inventors: Marcin Sikora, Redwood City, CA (US); Andrew Kennedy, La Jolla, CA (US); Ariel Jaimovich, Redwood City, CA (US); Darya Chudova, San Jose, CA (US); Stephen Fairclough, Redwood City, CA (US)

(73) Assignee: GUARDANT HEALTH, INC., Redwood City, CA (US)

( * ) Notice: Subject to any disclaimer, the term of this patent is extended or adjusted under 35 U.S.C. 154(b) by 0 days.

(21) Appl. No.: 16/866,252

(22) Filed: May 4, 2020

(65) Prior Publication Data

US 2020/0377941 A1   Dec. 3, 2020

Related U.S. Application Data

(63) Continuation of application No. PCT/US2018/059056, filed on Nov. 2, 2018.
(Continued)

(51) Int. Cl.
*C12Q 1/6874*   (2018.01)
*C12Q 1/6806*   (2018.01)
*C12Q 1/6869*   (2018.01)

(52) U.S. Cl.
CPC ......... *C12Q 1/6874* (2013.01); *C12Q 1/6806* (2013.01); *C12Q 1/6869* (2013.01)

(58) Field of Classification Search
CPC .. C12Q 1/6874; C12Q 1/6883; C12Q 1/6858; C12Q 2600/154; C12Q 1/6869;
(Continued)

(56) References Cited

U.S. PATENT DOCUMENTS 6,582,908 B2   6/2003   Fodor et al.
6,630,144 B1 *  10/2003  Hart ..................... A61P 31/14
                                                      424/159.1
(Continued)

FOREIGN PATENT DOCUMENTS

WO   2013142389 A1   9/2013
WO   2013191637 A1   12/2013
(Continued)

OTHER PUBLICATIONS

Arbeithuber et al. DNA Research. 2016. 23(6):547-559. (Year: 2016).*
(Continued)

*Primary Examiner* — Joseph G. Dauner
(74) *Attorney, Agent, or Firm* — Timothy A. Hott

(57) ABSTRACT

Sequencing nucleic acids can identify variations associated with presence, susceptibility or prognosis of disease. However, the value of such information can be compromised by errors introduced by or before the sequencing process including preparing nucleic acids for sequencing. Blunting single-stranded overhangs on nucleic acids in a sample can introduce deamination-induced sequencing errors. The disclosure provides methods of identifying and correcting for such deamination-induced sequencing errors and distinguishing them from real sequence variations.

29 Claims, 7 Drawing Sheets

Specification includes a Sequence Listing.

Related U.S. Application Data

(60) Provisional application No. 62/581,609, filed on Nov. 3, 2017.

(58) Field of Classification Search
CPC ........ C12Q 1/6837; B82Y 5/00; B82Y 15/00; G16B 20/20
See application file for complete search history.

(56) References Cited

U.S. PATENT DOCUMENTS

| | | |
|---|---|---|
| 7,537,898 B2 | 5/2009 | Bost et al. |
| 9,598,731 B2 | 3/2017 | Talasaz |
| 2001/0053519 A1 | 12/2001 | Fodor et al. |
| 2011/0160078 A1 | 6/2011 | Fodor et al. |
| 2015/0031559 A1 | 1/2015 | Casbon et al. |
| 2015/0044191 A1* | 2/2015 | Liu ................ C12Y 301/00 424/94.6 |
| 2015/0066385 A1 | 3/2015 | Schnall-Levin et al. |
| 2015/0087535 A1 | 3/2015 | Patel |
| 2017/0204459 A1 | 7/2017 | Barany et al. |
| 2018/0251848 A1 | 9/2018 | Diehn et al. |

FOREIGN PATENT DOCUMENTS

| | | |
|---|---|---|
| WO | 2014149134 A2 | 9/2014 |
| WO | 2015164432 | 12/2015 |

OTHER PUBLICATIONS

Sloan et al. Trends Biotechnol. 2018. 36(7)729-740. (Year: 2018).*
Salk et al. Nat Rev Genet. 2018. 19(5):269-285. (Year: 2018).*
Ma et al. Genome Biology. 2019. 20:50. (Year: 2019).*
Akre et al. "Mutation Processes in 293-Based Clones Overexpressing the DNA Cytosine Deaminase APOBEC38," PLoS One, May 10, 2016 (May 10, 2016), vol. 11, No. 5, 00155391, pp. 1-17. entire document.
Cannistraro, V.J. et al. "Rapid Deamination of Cyclobutane Pyrimidine Dimer Photoproducts at TCG Sites in a Translationally and Rotationally Positioned Nucleosome in Vivo" J. Bill Chem (2015) 290(44):26597-26609.
Chen et al. "DNA damage is a major cause of sequencing errors, directly confounding variant identification," bioRxiv, Aug. 23, 2016 (Aug. 23, 2016), pp. 1-30.
Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.
International search report and written opinion dated Jan. 17, 2019 for PCT/US2018/059056.
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.
Phallen, J. et al. "Direct detection of early-stage cancers using circulating tumor DNA" Sci Trans Med (2017) vol. 9, Issue 403, eaan2415DOI: 10.1126/scitranslmed.aan2415.
Siravegna, G. et al. "Integrating liquid biopsies into the management of cancer" Nature Reviews Clinical Oncology (2017)14:531-548.

* cited by examiner

SEQUENCE LISTING

<160> NUMBER OF SEQ ID NOS: 4

<210> SEQ ID NO 1
<211> LENGTH: 28
<212> TYPE: DNA
<213> ORGANISM: Homo sapiens

<400> SEQUENCE: 1
taccggcaga tccctttgcc tgcagggg                                    28

<210> SEQ ID NO 2
<211> LENGTH: 21
<212> TYPE: DNA
<213> ORGANISM: Homo sapiens

<400> SEQUENCE: 2
cctggcctgc gagggctctc a                                           21

```
<210> SEQ ID NO 3
<211> LENGTH: 14
<212> TYPE: DNA
<213> ORGANISM: Homo sapiens

<400> SEQUENCE: 3
agagcctttc cctc                                                   14

<210> SEQ ID NO 4
<211> LENGTH: 23
<212> TYPE: DNA
<213> ORGANISM: Homo sapiens

<400> SEQUENCE: 4
agagcctttc cctctgccct ttt                                         23
```

CORRECTING FOR DEAMINATION-INDUCED SEQUENCE ERRORS

CROSS-REFERENCE

This application is a continuation of International Application No. PCT/US2018/059056, filed Nov. 2, 2018, which claims priority to U.S. Provisional Application No. 62/581,609, filed Nov. 3, 2017, which such application is entirely incorporated herein by reference for all purposes.

SEQUENCE LISTING

The instant application contains a Sequence Listing which has been filed electronically in ASCII format and is hereby incorporated by reference in its entirety. Said ASCII copy, created on Jul. 15, 2020, is named GH0032US-CON_SL_1.txt and is 1,050 bytes in size.

BACKGROUND

A tumor is an abnormal growth of cells. Fragmented DNA is often released into bodily fluid when cells, such as tumor cells, die. Thus, some of the cell-free DNA in body fluids is tumor DNA. A tumor can be benign or malignant. A malignant tumor is often referred to as a cancer.

Cancer is a major cause of disease worldwide. Each year, tens of millions of people are diagnosed with cancer around the world, and more than half eventually die from it. In many countries, cancer ranks as the second most common cause of death following cardiovascular diseases. Early detection is associated with improved outcomes for many cancers.

Cancer is caused by the accumulation of mutations and/or epigenetic variations within an individual's normal cells, at least some of which result in improperly regulated cell division. Such mutations commonly include copy number variations (CNVs), copy number aberrations (CNA), single nucleotide variations (SNVs), gene fusions and indels, and epigenetic variations include modifications to the 5th atom of the 6-atom ring of cytosine and association of DNA with chromatin and transcription factors.

Cancers are often detected by biopsies of tumors followed by analysis of cells, markers or DNA extracted from cells. But more recently it has been proposed that cancers can also be detected from cell-free nucleic acids in body fluids, such as blood or urine (see, e.g., Siravegna et al., Nature Reviews 2017). Such tests have the advantage that they are non-invasive and can be performed without identifying suspected cancer cells through biopsy. However, such tests are complicated by the fact that the amount of nucleic acids in body fluids is very low and what nucleic acids are present require processing to a more homogenous form before sequencing can occur.

SUMMARY

One aspect of the disclosure relates to a method for identifying variant nucleotides in a population of nucleic acids comprising: (a) contacting a population of nucleic acids comprising double-stranded molecules with single-stranded overhangs at one or both ends with a protein having 5'-3' polymerase activity and a 3'-5' exonuclease activity, wherein the protein digests 3' overhangs and fills in 5' overhangs with complementary nucleic acids, to generate double-stranded blunt-ended nucleic acids at one or both ends; (b) determining sequences of the double-stranded blunt-ended nucleic acids to provide sequenced nucleic acids; (c) for each designated position in a reference sequence, (i) identifying a subset of sequenced nucleic acids including the designated position, and (ii) identifying sequenced nucleic acids in the subset in which the designated position is occupied by a variant nucleotide; and (d) calling presence of a variant nucleotide at each designated position at which the sequenced nucleic acids in the subset with the variation supports the call, except that presence of a variant nucleotide at a designated position is not called if: (i) the variant is a C to T or G to A variation compared with the reference nucleotide; and (ii) the variant nucleotide is categorized as a deamination error based on: (1) nucleotide context around the designated position and/or (2) distance of the C to T variation at the designated position from the 5'-end in sequenced nucleic acids in the subset or distance of the G to A variation at the designated position from the 3'-end in sequenced nucleic acids in the subset.

In some embodiments step (c)(ii) identifies the number of consensus sequences in the subset in which the designated position is occupied by a variant nucleotide and presence of a variant nucleotide at each designated position is called when the number of consensus sequences in the subset with the variation meets a threshold except as specified in steps (d)(i) and (ii).

In some embodiments, the variant nucleotide is categorized as a deamination error based on the representation of the C to T variation at the designated position within a defined proximity of the 5'-end in sequenced nucleic acids in the subset or representation of the G to A variation at the designated position within a defined proximity of the 3'-end in sequenced nucleic acids in the subset.

In some embodiments, (c)(ii) further comprises identifying the number of sequenced nucleic acids in the subset in which the designated position is occupied by a reference nucleotide.

In some embodiments, (b) comprises determining sequences of both strands of the double-stranded blunt-ended nucleic acid.

In some embodiments, (c) is performed for at least one designated position wherein the sequenced nucleic acids in the subset with the variation include sequences of both strands of the double-stranded blunt-ended nucleic acid sequenced nucleic acid.

In some embodiments, (b) comprises determining sequences from both ends of a strand.

In some embodiments, the method further comprises linking the double-stranded blunt-ended nucleic acids to adapters comprising barcodes, amplifying the nucleic acids primed from primer molecules binding to the adapters, wherein (b) comprises determining sequences of amplified nucleic acid molecules and classifying the sequences of the amplified nucleic acid molecules into families, the members of a family having the same start and stop points on the nucleic acid and the same barcodes, and determining consensus nucleotides at each of a plurality of positions for the families from the sequences of their respective members. The consensus sequences are not determined for families having only one member.

In some embodiments, the population of nucleic acids are from a cell-free nucleic acid sample of a subject. The cell-free nucleic acid sample can be from a body fluid of a subject having a cancer or having signs or symptoms consistent with having a cancer. The body fluid can be selected from the group consisting of blood, plasma, saliva, urine, and cerebrospinal fluid. Blood and blood products (e.g.

plasma and serum) contain cell-free nucleic acids which are particularly useful for use as described herein.

In some embodiments, the C to T variation at the designated position is classified as a deamination error if its representation is at least 50% in a first fraction of the subset in which the designated position is within a defined proximity of the 5' end or the G to A variation at the designated position is classified as a deamination error if its representation is at least 50% in a second fraction of the subset in which the designated position is within a defined proximity of the 3' end. The C to T variation at the designated position can be classified as a deamination error based on the variation having at least twice the representation in a first fraction of the subset in which the designated position is within a defined proximity of the 5' end than in other sequenced nucleic acid in the subset, or the G to A variation at the designated position is classified as a deamination error based on the variation having at least twice the representation in a second fraction of the subset in which the designated position is within a defined proximity to the 3' end than in other sequenced nucleic acids in the subset.

In some embodiments, the threshold is that the variation is present in at least 1% of sequenced nucleic acids in the subset.

In some embodiments, the C to T or G to A variation is categorized as a deamination error at least based on the surrounding context being TCG to TTG or CGA to CAA.

In some embodiments, the defined proximity to the 5' end is defined as being within 20 nucleotides or within a fewer number of nucleotides to the 5' end and the defined proximity to the 3' end is defined as being within 20 nucleotides or within a fewer number of nucleotides to the 3' end. The defined proximity to the 5' end can be defined as being within 20 nucleotides to the 5' end and the defined proximity to the 3' end is defined as being within 20 nucleotides to the 3' end.

In some embodiments, the protein is Klenow.

In some embodiments, (c) and (d) are performed in a computer-operated system or the like to carry out these steps. In these embodiments, therefore, the disclosure relates to a computer-implemented method for identifying variant nucleotides in a population of nucleic acids.

In some embodiments, the reference sequence is a sequence of a human genome. The reference sequence can be a sequence of a human chromosome. The reference sequence can comprise noncontiguous regions of a human genome.

In some embodiments, at least one of the variant nucleotides called is known to be associated with a cancer.

In some embodiments, the method can be performed on nucleic acid populations from samples from a population of subjects having or suspected of having a cancer, wherein subjects in the population thereafter receive different treatments depending on which variant nucleotides are called in the individual subject.

In some embodiments, variant nucleotides classified as deamination errors are at least 1% of the called variant nucleotides.

In some embodiments, variant nucleotides classified as deamination errors are at least 10% of the called variant nucleotides.

In some embodiments, the presence of a variant is not called if at least 5 variant nucleotides are classified as deamination errors.

In some embodiments, the population of nucleic acids are derived from a solid tissue.

In some embodiments, the body fluid is plasma.

In some embodiments, the adapters comprising barcodes linked to the 5' ends are different from the adapters comprising barcodes linked to the 3'-end.

In some embodiments, a frequency of the deamination error is at least 1%.

In some embodiments, a frequency of the deamination error is at least 10%.

In some embodiments, the variant nucleotide is categorized as a deamination error based on the average distance of the C to T variation at the designated position being less than the average distance of the reference nucleotide at the designated position from the 5'-end of sequenced nucleic acids in the subset or the G to A variation at the designated position being less than the average distance of the reference nucleotide at the designated position from the 3'-end of sequenced nucleic acids in the subset.

In some embodiments, the variant nucleotide is a single nucleotide variant (SNV).

One aspect of the disclosure relates to a method identifying variant nucleotides in a nucleic acid, comprising: (a) contacting a double-stranded nucleic acid with single-stranded overhangs with a protein having 5'-3' polymerase activity and a 3'-5' exonuclease activity thereby producing a double-stranded blunt-ended nucleic acid; (b) determining a sequence of the double-stranded blunt-ended nucleic acid; (c) comparing the determined sequence to a reference sequence, wherein the determined sequence includes at least one C to T variation in at least one designated position within 20 nucleotides or fewer of the 5' end of the determined sequence or at least one G to A variation within 20 nucleotides or fewer of the 3' end of the determined sequence; (d) calling a sequence for the nucleic acid as the determined sequence except in at least one of the positions in which a C to T variation is present within 20 nucleotides or fewer of the 5' end of the determined sequence or a G to A variation within 20 nucleotides or fewer of the 3' end of the determined sequence, where the nucleotide occupying the reference sequence is called at the designated position.

In some embodiments, the C to T or G to A variation occurs in a surrounding context of TCG to TTG or CGA to CAA.

One aspect of the disclosure relates to a method identifying variant nucleotides in a population of nucleic acids comprising: (a) contacting a population of nucleic acids of overlapping sequences at least one of which is a double-stranded molecule with single-stranded overhangs at one or both ends with a protein having 5'-3' polymerase activity and a 3'-5' exonuclease activity, wherein the protein digests 3' overhangs and fills in 5' overhangs to generate double-stranded blunt-ended nucleic acids; (b) linking the double-stranded blunt-ended nucleic acids to adapters comprising barcodes, amplifying the nucleic acids primed from primer molecules binding to the adapters, wherein (c) determining sequences of amplified nucleic acid molecules and classifying the sequences of the amplified nucleic acid molecules into families, the members of a family having the same start and stop points on the nucleic acid and the same adapters, and determining consensus sequences for the families from the sequences of their respective members; (d) for each designated position in a reference sequence determining a subset of families having a consensus sequence including the designated position and identifying the consensus sequences in which the designated position is occupied by a variant nucleotide; and (e) calling presence of a variant nucleotide at each designated position at which the consensus sequences in the subset with the variant nucleotide support the call except that presence of a variant nucleotide at a designated position is not called if: (i) the variant nucleotide is a C to T or G to A variation compared with the reference nucleotide; and (ii) the variant nucleotide is categorized as a deamination error based on: (1) nucleotide context around the designated position and/or (2) distance of the C to T variation at the designated position in consensus sequences in the subset from the 5' end or distance of the G to A variation at the designated position in consensus sequences from the 3' end.

In some embodiments, step (c) identifies the number of consensus sequences in the subset in which the designated position is occupied by a variant nucleotide and presence of a variant nucleotide at each designated position is called when the number of consensus sequences in the subset with the variation meets a threshold except as specified in steps (d)(i) and (ii).

In one aspect, the disclosure relates to a method for identifying false positive variant nucleotides in a population of nucleic acids comprising: (a) contacting a population of nucleic acids at least one of which is a double-stranded molecule with single-stranded overhangs at one or both ends and overlapping sequences with a protein having 5'-3' polymerase activity and a 3'-5' exonuclease activity, wherein the protein digests 3' overhangs and fills in 5' overhangs with complementary nucleic acids to generate double-stranded blunt-ended nucleic acids at one or both ends; (b) determining sequences of the double-stranded blunt-ended nucleic acids to provide sequenced nucleic acids (c) for each designated position in a reference sequence, identifying a subset of sequenced nucleic acids including the designated position and identifying sequenced nucleic acids in the subset in which the designated position is occupied by a reference nucleotide and the sequenced nucleic acids in the subset in which the designated position is occupied by a variant nucleotide; and (d) calling presence of a false positive variant nucleotide at each designated position at which the sequenced nucleic acids with a C to T or G to A variation at the designated position support the call and the variation is categorized as a deamination error based on: (1) nucleotide context around the designated position and/or (2) overrepresentation of the C to T conversion in sequenced nucleic acids within a first fraction of the subset in which the designated position is within a defined proximity of the 5' end or overrepresentation of the G to A conversion in sequenced nucleic acids in a second fraction of the subset in which the designated position is within a defined proximity of the 3' end.

In some embodiments, step (c) identifies the number of consensus sequences in the subset in which the designated position is occupied by a variant nucleotide and presence of a variant nucleotide at each designated position is called when the number of consensus sequences in the subset with the variation meets a threshold except as specified in steps (d)(i) and (ii).

In one aspect, the disclosure relates to a method of determining minor allele frequency of a "C" to "T" or a "G" to "A" variant at a designated position in a reference sequence in a population of sequenced nucleic acids mapping to the designated position, wherein minor allele frequency compares a number of sequenced nucleic acids mapping to the designated position comprising the variant ("variant number") to a total number of sequenced nucleic acids mapping to the designated position, the method comprising adjusting the variant number of T or A variants at the designated position for probability of deamination errors, wherein probability of error is a function of distance of the variant from a 5' terminus of a molecule in the case of "T" and from the 3' end of the molecule in case of "A".

In some embodiments, a C to T variant positioned within a selected distance from the 5' end of a sequenced polynucleotide, or a G to A variant positioned within a selected distance from the 3' end of a sequenced nucleic acid, is not counted in the variant number.

In some embodiments, wherein all C to T variants are discounted from the variant number when the ratio of C to T variants positioned within a selected distance from the 5' end of a sequenced polynucleotide to C to T variants positioned outside the selected distance from the 5' end of a sequenced nucleic acid is greater than a predetermined ratio (e.g., greater than 50%), or when the ratio of G to A variants positioned within a selected distance from the 3' end of a sequenced nucleic acid to G to A variants positioned outside the selected distance from the 3' end of a sequenced nucleic acid is greater than a predetermined ratio (e.g., greater than 50%).

In some embodiments, the variant number is determined as the sum of probabilities that each C to T variant or each G to A variant is a true variant.

In one aspect, the disclosure relates to a method comprising administering to a subject determined to have cancer marker by the method of any of the previous claims, a therapeutic intervention effective to treat a cancer characterized by the cancer marker.

The disclosure further provides a method comprising receiving data for the identity of one or more variant nucleotides in cell free nucleic acids of a subject by performing a method of any of the preceding claims; determining presence of a cancer marker from the one or more variant nucleotides; and administering a therapeutic intervention effective to treat a cancer characterized by the cancer marker.

In another aspect, the disclosure relates to a system.
(1) One such system comprises:
(2) a communication interface that receives, over a communication network, sequencing reads generated by a nucleic acid sequencer; and
(3) a computer in communication with the communication interface, wherein the computer comprises one or more computer processors and a computer readable medium comprising machine-executable code that, upon execution by the one or more computer processors, implements a method comprising:
  (a) receiving, over the communication network, the sequencing reads generated by the nucleic acid sequencer;
  (b) for each designated position in a reference sequence,
    (i) identifying a subset of sequencing reads including the designated position, and
    (ii) identifying sequencing reads in the subset in which the designated position is occupied by a variant nucleotide; and
  (c) calling presence of a variant nucleotide at each designated position at which the sequencing reads in the subset with the variation support the call, except that presence of a variant nucleotide at a designated position is not called if:
    (i) the variant is a C to T or G to A variation compared with the reference nucleotide; and
    (ii) the variant nucleotide is categorized as a deamination error based on:
      (1) nucleotide context around the designated position and/or (2) distance of the C to T variation at the designated position from the 5'-end in sequenced nucleic acids in the subset or distance of the G to A variation at the designated position from the 3'-end in sequenced nucleic acids in the subset.

In some embodiments, step (c) identifies the number of consensus sequences in the subset in which the designated position is occupied by a variant nucleotide and presence of a variant nucleotide at each designated position is called when the number of consensus sequences in the subset with the variation meets a threshold except as specified in steps (d)(i) and (ii).

The disclosure further provides a system, comprising:
(1) a communication interface that receives, over a communication network, sequencing reads generated by a nucleic acid sequencer; and
(2) a computer in communication with the communication interface, wherein the computer comprises one or more computer processors and a computer readable medium comprising machine-executable code that, upon execution by the one or more computer processors, implements a method comprising:
  (a) receiving, over the communication network, the sequencing reads generated by the nucleic acid sequencer;
  (b) comparing the determined sequence to a reference sequence, wherein the determined sequence includes at least one C to T variation in at least one designated position within 20 nucleotides or fewer of the 5' end of the determined sequence or at least one G to A variation within 20 nucleotides or fewer of the 3' end of the determined sequence; and
  (c) calling a sequence for the nucleic acid as the determined sequence except in at least one of the positions in which a C to T variation is present within 20 nucleotides or fewer of the 5' end of the determined sequence or a G to A variation within 20 nucleotides or fewer of the 3' end of the determined sequence, where the nucleotide occupying the reference sequence is called at the designated position.

The disclosure further provides a system, comprising:
(1) a communication interface that receives, over a communication network, sequencing reads generated by a nucleic acid sequencer; and
(2) a computer in communication with the communication interface, wherein the computer comprises one or more computer processors and a computer readable medium comprising machine-executable code that, upon execution by the one or more computer processors, implements a method comprising:
  (a) receiving, over the communication network, the sequencing reads generated by the nucleic acid sequencer;
  (b) classifying the sequences of the sequencing reads into families, the members of a family having the same start and stop points on the nucleic acid and the same adapters, and determining consensus sequences for the families from the sequences of their respective members;
  (c) for each designated position in a reference sequence determining a subset of families having a consensus sequence including the designated position and identifying the consensus sequences in which the designated position is occupied by a variant nucleotide; and
  (d) calling presence of a variant nucleotide at each designated position at which the consensus sequences in the subset with the variant nucleotide support the call except that presence of a variant nucleotide at a designated position is not called if:
    (i) the variant nucleotide is a C to T or G to A variation compared with the reference nucleotide; and
    (ii) the variant nucleotide is categorized as a deamination error based on:
      (1) nucleotide context around the designated position and/or
      (2) distance of the C to T variation at the designated position in consensus sequences in the subset from the 5' end or distance of the G to A variation at the designated position in consensus sequences from the 3' end.

In some embodiments, step (c) identifies the number of consensus sequences in the subset in which the designated position is occupied by a variant nucleotide and presence of a variant nucleotide at each designated position is called when the number of consensus sequences in the subset with the variation meets a threshold except as specified in steps (d)(i) and (ii)

The disclosure further provides a system, comprising:
(1) a communication interface that receives, over a communication network, sequencing reads generated by a nucleic acid sequencer; and
(2) a computer in communication with the communication interface, wherein the computer comprises one or more computer processors and a computer readable medium comprising machine-executable code that, upon execution by the one or more computer processors, implements a method comprising:
  (a) receiving, over the communication network, the sequencing reads generated by the nucleic acid sequencer;
  (b) for each designated position in a reference sequence, identifying a subset of sequencing reads including the designated position and identifying the sequenced nucleic acids in the subset in which the designated position is occupied by a reference nucleotide and the sequenced nucleic acids in the subset in which the designated position is occupied by a variant nucleotide; and
  (c) calling presence of a false positive variant nucleotide at each designated position at which the sequenced nucleic acids with a C to T or G to A variation at the designated position support the call and the variation is categorized as a deamination error based on:
    (1) nucleotide context around the designated position and/or
    (2) overrepresentation of the C to T conversion in sequenced nucleic acids within a first fraction of the subset in which the designated position is within a defined proximity of the 5' end or overrepresentation of the G to A conversion in sequenced nucleic acids in a second fraction of the subset in which the designated position is within a defined proximity of the 3' end.

In some embodiments, step (c) identifies the number of consensus sequences in the subset in which the designated position is occupied by a variant nucleotide and presence of a variant nucleotide at each designated position is called when the number of consensus sequences in the subset with the variation meets a threshold except as specified in steps (d)(i) and (ii).

The disclosure further provides a system, comprising:
(1) a communication interface that receives, over a communication network, sequencing reads generated by a nucleic acid sequencer; and (2) a computer in communication with the communication interface, wherein the computer comprises one or more computer processors and a computer readable medium comprising machine-executable code that, upon execution by the one or more computer processors, implements a method comprising:

(a) receiving, over the communication network, the sequencing reads generated by the nucleic acid sequencer;

(b) adjusting the number of T or A variants in the sequencing reads based on a probability of deamination errors, wherein probability of error is a function of distance of the variant from a 5' terminus of a molecule in the case of "T" and from the 3' end of the molecule in case of "A".

Any of the above systems can further include a nucleic acid sequencer. Optionally, the nucleic acid sequencer sequences a sequencing library generated from cell-free DNA molecules derived from a subject, wherein the sequencing library comprises the cell-free DNA molecules and adapters, wherein the adapters comprise barcodes. Optionally, the nucleic acid sequencer performs sequencing-by-synthesis on the sequencing library to generate the sequencing reads. Optionally, the nucleic acid sequencer performs pyrosequencing, single-molecule sequencing, nanopore sequencing, semiconductor sequencing, sequencing-by-ligation or sequencing-by-hybridization on the sequencing library to generate the sequencing reads. Optionally, the nucleic acid sequencer uses a clonal single molecule array derived from the sequencing library to generate the sequencing reads. Optionally, the nucleic acid sequencer comprises a chip having an array of microwells for sequencing the sequencing library to generate the sequencing reads.

In some systems, the computer readable medium comprises a memory, a hard drive or a computer server. In some systems, the communication network comprises a telecommunication network, an internet, an extranet, or an intranet. In some systems, the communication network includes one or more computer servers capable of distributed computing, such as cloud computing. In some systems, the computer is located on a computer server that is remotely located from the nucleic acid sequencer. In some systems, the sequencing library further comprises sample barcodes that differentiate a sample from one or more samples.

Some systems further comprise an electronic display in communication with the computer over a network, wherein the electronic display comprises a user interface for displaying results upon implementing (a)-(c), such as a graphical user interface (GUI) or web-based user interface. In some systems, the electronic display is in a personal computer. In some systems, the electronic display is in an internet enabled computer, optionally at a location remote from the computer.

In some embodiments, the results of the systems and methods disclosed herein are used as an input to generate a report in a paper format. For example, this report may provide an indication of the called variants and/or the variants which are deemed to be deamination errors.

The various steps of the methods disclosed herein, or the steps carried out by the systems disclosed herein, may be carried out at the same or different times, in the same or different geographical locations, e.g. countries, and/or by the same or different people.

DEFINITIONS

Figure 1:
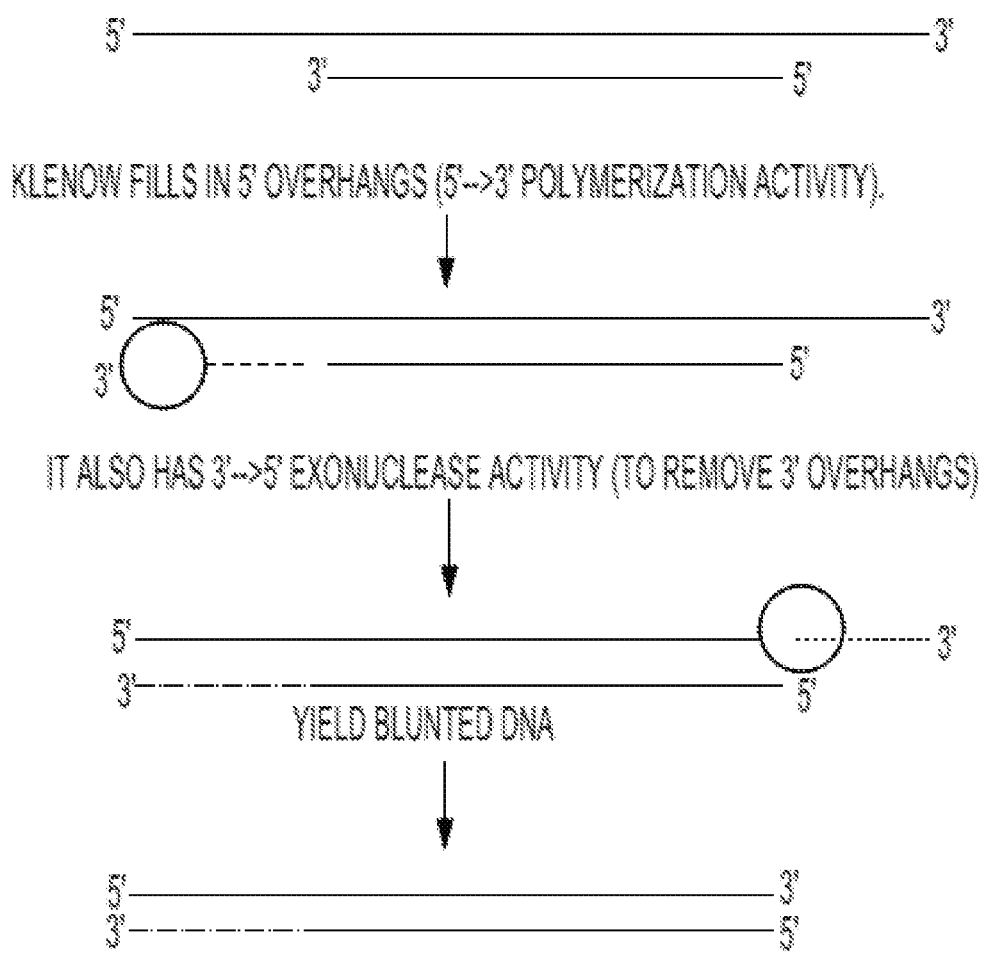
FIG. 1 shows an overview of end repair with Klenow polymerase.

A subject refers to an animal, such as a mammalian species (preferably human) or avian (e.g., bird) species, or other organism, such as a plant. More specifically, a subject can be a vertebrate, e.g., a mammal such as a mouse, a primate, a simian or a human. Animals include farm animals, sport animals, and pets. A subject can be a healthy individual, an individual that has symptoms or signs or is suspected of having a disease or a predisposition to the disease, or an individual that is in need of therapy or suspected of needing therapy.

A genetic variant refers to an alteration, variant or polymorphism in a nucleic acid sample or genome of a subject. Such alteration, variant or polymorphism can be with respect to a reference genome, which may be a reference genome of the species (e.g., for human, hG19 or hG38), the subject or other individual. Variations include one or more single nucleotide variations (SNVs), insertions, deletions, repeats, small insertions, small deletions, small repeats, structural variant junctions, variable length tandem repeats, and/or flanking sequences, copy number variants (CNVs), transversions, gene fusions and other rearrangements are also forms of genetic variation. A variation can be a base change, insertion, deletion, repeat, copy number variation, transversion, or a combination thereof.

A cancer marker is a genetic variant associated with presence or risk of developing a cancer. A cancer marker can provide an indication a subject has cancer or a higher risk of developing cancer than an age and gender matched subject of the same species that does not have the cancer marker. A cancer marker may or may not be causative of cancer.

A barcode is a short nucleic acid (e.g., less than 500, 100, 50 or 10 nucleotides long), used to label nucleic acid molecules to distinguish nucleic acids from different samples (e.g., representing a sample index), or different nucleic acid molecules in the same sample (e.g., representing a barcode), of different types, or which have undergone different processing. Tags can be single stranded, double-stranded or at least partially double-stranded. Tags can have the same length or varied lengths. Tags can be blunt-end or have an overhang. Tags can be attached to one end or both ends of the nucleic acids. Barcodes can be decoded to reveal information such as the sample of origin, form or processing of a nucleic acid. Tags can be used to allow pooling and parallel processing of multiple samples comprising nucleic acids bearing different barcodes and/or sample indexes with the nucleic acids subsequently being deconvoluted by reading the barcodes. Barcodes can also be referred to as molecular identifiers, sample identifier, index tag, and/or tags. Additionally or alternatively, barcodes can be used to distinguish different molecules in the same sample. This includes uniquely barcoding each different molecule in the sample, or non-uniquely barcoding each molecule. In the case of non-unique barcoding, a limited number of barcodes may be used to barcode each molecule such that different molecules can be distinguished based on their start/stop position where they map on a reference genome in combination with at least one tag. Typically then, a sufficient number of different barcodes are used such that there is a low probability (e.g. <10%, <5%, <1%, or <0.1%) that any two molecules having the same start/stop also have the same barcode. Some barcodes include multiple molecular identifiers to label samples, forms of molecule within a sample, and molecules within a form having the same start and stop points. Such barcodes can exist in the form Ali, wherein the letter indicates a sample type, the Arabic number indicates a form of molecule within a sample, and the Roman numeral indicates a molecule within a form.

Adapters are short nucleic acids (e.g., less than 500, 100 or 50 nucleotides long) usually at least partly double-stranded for linkage to either or both ends of a sample nucleic acid molecule. Adapters can include primer binding sites to permit amplification of a nucleic acid molecule flanked by adapters at both ends, and/or a sequencing primer binding site, including primer binding sites for next generation sequencing (NGS). Adapters can also include binding sites for capture probes, such as an oligonucleotide attached to a flow cell support. Adapters can also include a barcode as described above. Barcodes are preferably position relative to primer and sequencing primer binding sites, such that a barcode is included in amplicons and sequencing reads of a nucleic acid molecule. The same or different adapters can be linked to the respective ends of a nucleic acid molecule. Sometimes the same adapter is linked to the respective ends except that the barcode is different. A preferred adapter is a Y-shaped adapter in which one end is blunt ended or tailed as described herein, for joining to a nucleic acid molecule, which is also blunt ended or tailed with one or more complementary nucleotides. Another preferred adapter is a bell-shaped adapter, likewise with a blunt or tailed end for joining to a nucleic acid to be analyzed.

As used herein, the term "sequencing" refers to any of a number of technologies used to determine the sequence of a biomolecule, e.g., a nucleic acid such as DNA or RNA. Exemplary sequencing methods include, but are not limited to, targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performed by a gene analyzer such as, for example, gene analyzers commercially available from Illumina or Applied Biosystems.

The phrase "next generation sequencing" or NGS refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

The phrase "sequencing run" refers to any step or portion of a sequencing experiment performed to determine some information relating to at least one biomolecule (e.g., a nucleic acid molecule such as DNA or RNA).

DNA (deoxyribonucleic acid) is a chain of nucleotides comprising four types of nucleotides; adenine (A), thymine (T), cytosine (C), and guanine (G). RNA (ribonucleic acid) is a chain of nucleotides comprising four types of nucleotides; A, uracil (U), G, and C. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "nucleotide sequence", "genomic sequence," "genetic sequence," or "fragment sequence," or "nucleic acid sequencing read" denotes any information or data that is indicative of the order of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

A "polynucleotide", "nucleic acid", "nucleic acid molecule", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'→3' order from left to right and that "A"

denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

A reference sequence is a known sequence used for purposes of comparison with experimentally determined sequences. For example, a known sequence can be an entire genome, a chromosome, or any segment thereof. A reference typically includes at least 20, 50, 100, 200, 250, 300, 350, 400, 450, 500, 1000, or more nucleotides. A reference sequence can align with a single contiguous sequence of a genome or chromosome or can include noncontiguous segments aligning with different regions of a genome or chromosome. Reference human genomes include, e.g., hG19 and hG38.

The term "designated position" in a reference sequence refers to a genomic coordinate in the reference sequence.

A first single stranded nucleic acid sequence overlaps with a second single stranded sequence if the first nucleic acid sequence or its complement and the second nucleic acid sequence or its complement align with overlapping but non-identical segments of a contiguous reference sequence, such as the sequence of a human chromosome. A fully or partially double-stranded nucleic acid overlaps with another fully or partially double-stranded nucleic acid if either of its strands overlaps those of the other nucleic acid.

A "C" to "T" variant or conversion refers to the presence of base "T" in a sequenced polynucleotide at a coordinate position occupied in a reference sequence by base "C". A "G" to "A" variant or conversion refers to the presence of base "A" in a sequenced polynucleotide at a coordinate position occupied in a reference sequence by base "G".

A nucleic acid molecule can be conceptually divided into a 5' terminal end, an internal portion and a 3' terminal end. Terminal ends can be designated based a predetermined number of nucleotides from the terminus. For example, the 5' terminal end be represented by, e.g., the 20 terminal nucleotides to the 5' end. The 3' terminal end be represented by, e.g., the 20 terminal nucleotides to the 3' end. Alternatively, the nucleic acid molecule can be divided into a terminal portion, as described, and a remainder.

The term "minor allele frequency" refers to the frequency at which minor alleles (e.g., not the most common allele) occurs in a given population of nucleic acids, such as a sample. Genetic variants at a low minor allele frequency may have a relatively low frequency of presence in a sample.

A "minor allele fraction" (MAF) refers to the fraction of DNA molecules harboring an allelic alteration in a given sample. A MAF of a somatic variant can be less than 0.5, 0.1, 0.05, or 0.01. For example, a MAF of a somatic variant is <0.05.

The terms "processing", "calculating", and "comparing" can be used interchangeably. The term can refer to determining a difference, e.g., a difference in number or sequence. For example, gene expression, copy number variation (CNV), indel, and/or single nucleotide variant (SNV) values or sequences can be processed.

Adapters are an artificially synthesized sequence that can be coupled to a nucleic acid molecule or a polynucleotide sequence by any approach including ligation, hybridization, and/or amplification. Adapters are short nucleic acids (e.g., less than 500, 100 or 50 nucleotides long) usually at least partly double-stranded for linkage to either or both ends of a sample nucleic acid molecule. Adapters can include primer binding sites to permit amplification of a nucleic acid molecule flanked by adapters at both ends, and/or a sequencing primer binding site, including primer binding sites for next generation sequencing (NGS). Adapters can also include binding sites for capture probes, such as an oligonucleotide attached to a flow cell support. Adapters can also include a barcode as described above. Tags are preferably position relative to primer and sequencing primer binding sites, such that a tag is included in amplicons and sequencing reads of a nucleic acid molecule. The same or different adapters can be linked to the respective ends of a nucleic acid molecule. Sometimes the same adapter is linked to the respective ends except that the tag is different. A preferred adapter is a Y-shaped adapter in which one end is blunt ended or tailed as described herein, for joining to a nucleic acid molecule, which is also blunt ended or tailed with one or more complementary nucleotides. Another preferred adapter is a bell-shaped adapter, likewise with a blunt or tailed end for joining to a nucleic acid to be analyzed.

DETAILED DESCRIPTION

I. General

Sequencing nucleic acids can identify variations associated with the presence, susceptibility or prognosis of disease. However, the value of such information can be compromised by errors introduced by the sequencing process including preparing nucleic acids for sequencing or by other factors, such as environmental conditions which affect the quality of the sample of nucleic acids during transportation and/or initial laboratory processing. Environmental conditions affecting quality include temperature and length of storage period before processing. The disclosure is premised in certain aspects on the observation that blunting single-stranded overhangs on nucleic acids in a sample has a significant propensity for introducing deamination-induced sequencing errors in which a cytosine (C) is changed to thymine (T) at the 5' end of a nucleic acid strand resulting in a guanine (G) to adenine (A) change in the complementary base at the 3'-end of the complementary nucleic acid strand. The disclosure provides methods of identifying such deamination-induced sequencing errors and distinguishing them from real sequence variations, which may be associated with cancer or other disease.

II. Methods of Identifying and Correcting for Deamination-Induced Errors

Nucleic acids can be subject to deamination in which base "C" is converted to base "T". In this case, in a double-stranded molecule, one strand will have "T", and the complementary strand will have "G". Such errors can be detected upon sequencing if the sequences of the different strands are tracked.

The method can be performed on any nucleic acid that is partially double-stranded with at least one single-stranded overhang or a population including such a nucleic acid. Typically the method is performed on a population of nucleic acids at least some of which are partially double-stranded with single-stranded overhangs at one or both ends. The methods can be performed for example, on a population including at least 2, 10,000, 1,000,000, 1,000,000,000, 10,000,000,000 or more different such nucleic acids. Usually at least some nucleic acids including those with single-stranded overhangs in the population are of overlapping sequence. Such populations can exist naturally or as a result of fragmentation during preparation of a sample or can be generated enzymatically such as by partial restriction digestion.

A preferred form of nucleic acid population is cell-free nucleic acids such as exist in blood and other body fluids.

Such nucleic acids are typically in heterogeneous form including double-stranded DNA with single-stranded overhangs at one or both ends, as well as single-stranded DNA and RNA. Double-stranded blunt-ended DNA can also be present.

The nucleic acid population can be prepared for sequencing by enzymatic blunt-ending of double-stranded nucleic acids with single-stranded overhangs at one or both ends. The population can be treated with a protein with a 5'-3' DNA polymerase activity and a 3'-5' exonuclease activity in the presence of nucleotides (e.g., A, C, G and T or U). Exemplary proteins are DNA polymerases, such as Klenow large fragment and T4 DNA polymerase. At 5' overhangs, the protein extends the recessed 3' end on the complementary strand until it is flush with the 5' end producing a blunt end. At 3' overhangs, the protein digests from the 3' end up to and sometimes beyond the 5' end of the opposing strand. If digestion proceeds beyond the 5' end of the opposing strand, the gap can be filled in by polymerase activity as for a 5' overhang. Blunt-ending of double-stranded nucleic acids facilitates attachment of adapters and subsequent amplification.

Figure 2:
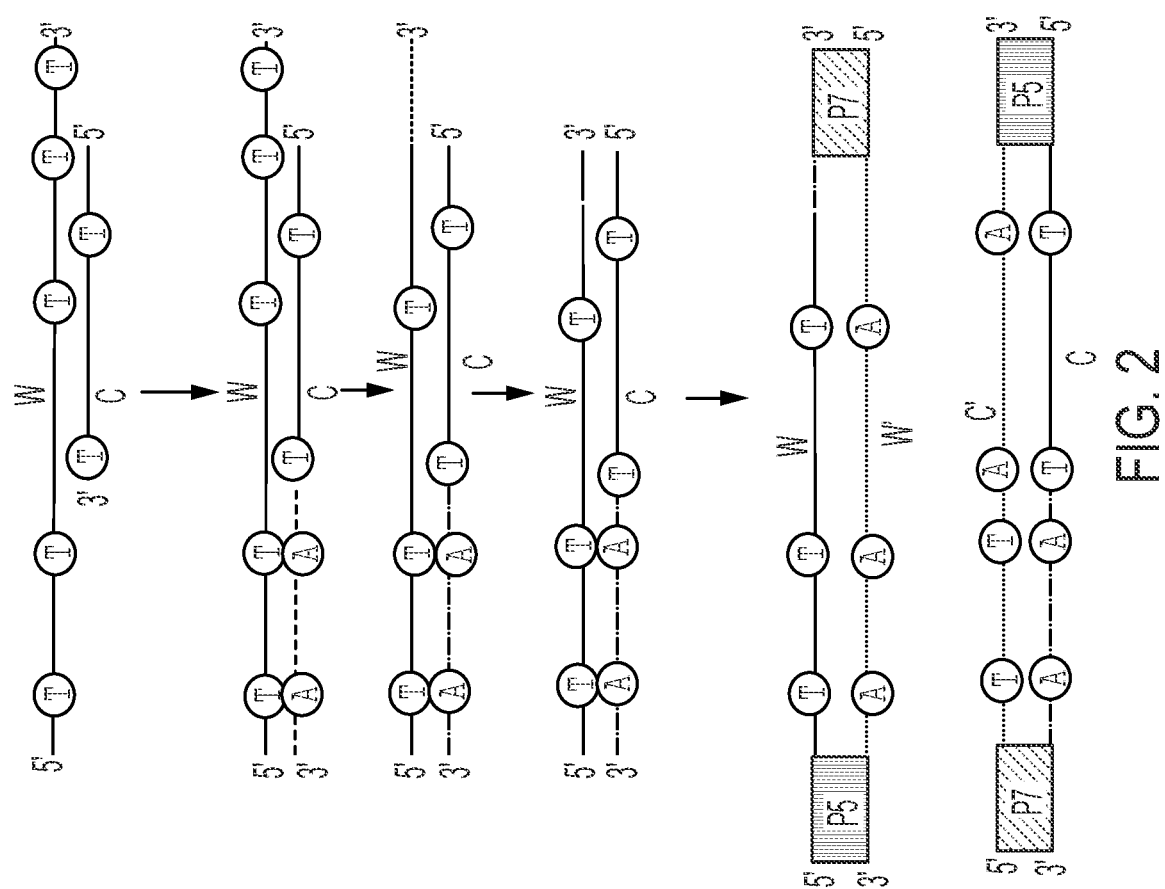
FIG. 2 shows a C→T deamination scheme.
Figure 3:
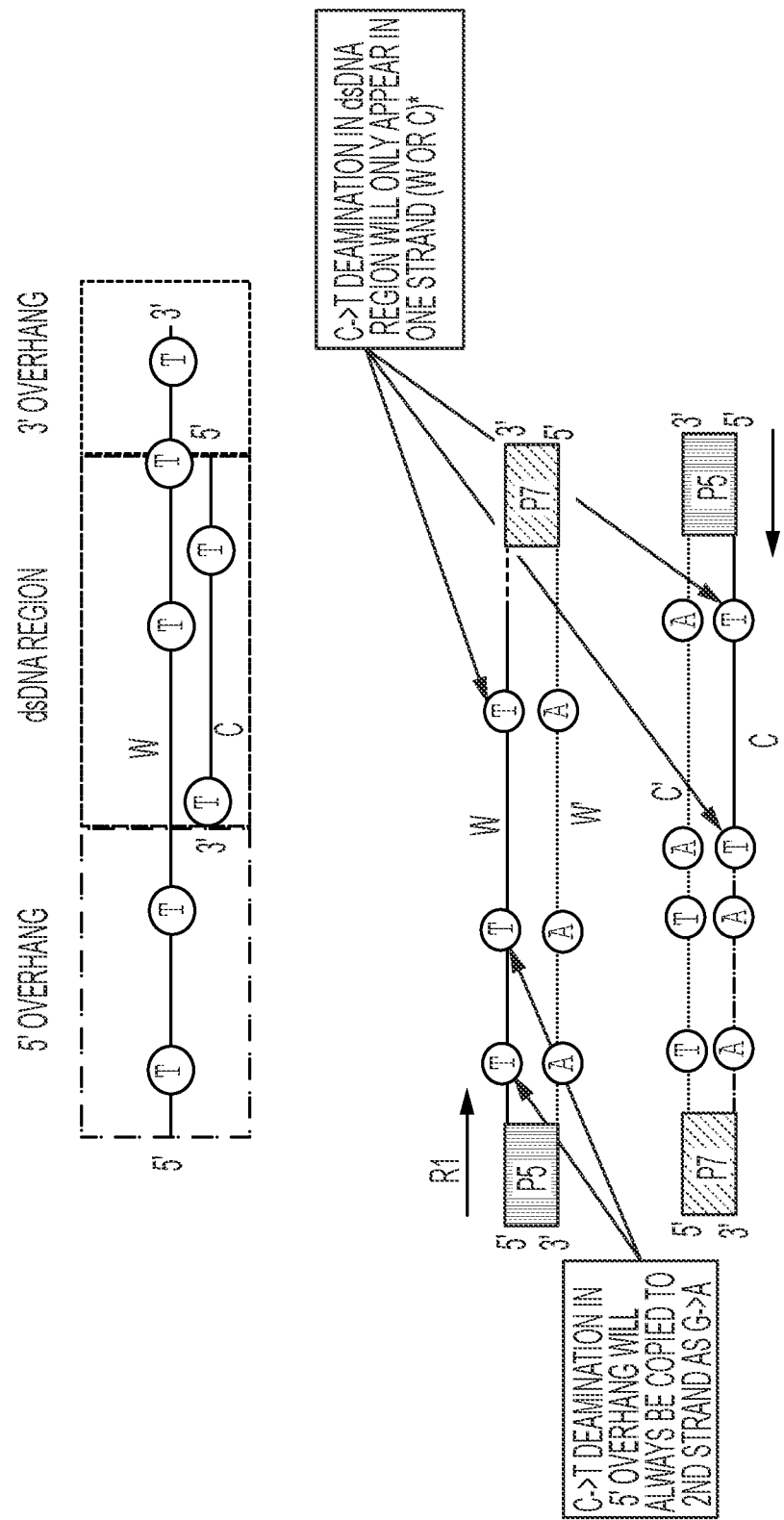
FIG. 3 shows preference of C→T conversion at 5' end of molecule and G→A conversion at 3' end of molecule.

However, the blunt ending process can also introduce deamination errors as shown in FIGS. 1-3. FIG. 1 shows a scheme by which a Klenow enzyme fills in 5' overhangs and digests 3' overhangs. FIGS. 2 and 3 show a scheme in which C-T deamination-induced errors are introduced at the 5'-end of a Watson strand and complementary G-A errors at the 3' end of the complementary Crick strand. Deamination-induced C to T conversions are shown by the circled T's. The circled A's represent corresponding changes in the complementary strand. Deamination induced errors in the 5' Watson strand are reproduced as a complementary nucleotide to the 3' end of the Crick strand due to extension of the 3' end based on the 5' overhang of Watson strand, e.g., a C to T conversion on the Watson strand and a G to A conversion on the Crick strand. Deamination-induced errors in the double-stranded region are not reproduced by way of the filling or digesting processes, and the two strands have non-complementary nucleotides at that position or nucleotide. Deamination-induced errors in the 3' end of the Watson strand are digested away. Deamination-induced errors near the 5' end of the Crick strand may be retained if the 3' end of the Watson strand is digested back so as to require fill-in of the nucleotide complementary to the deamination-induced error. In some embodiments, only C to T variations at the 5' end of a strand and G to A variations at the 3' end of a strand are represented in both strands of a nucleic acid molecule.

Accordingly, in the end-repaired, double-stranded molecule, a "C" to "T" conversion positioned at a 5' overhang in the Watson strand of the original molecule will be represented by a T error, and propagated in all amplified molecules as A on the complementary strands. A "C" to "T" conversion positioned at a double-stranded portion of the original molecule will be represented by G on one strand, and as A on the complementary strand. During amplification, the error is likely to be propagated as "T" on one strand, e.g., the Watson strand, and a mixture of "A" and "G" at the same position on the complementary strand, e.g., the Crick strand. A "C" to "T" conversion positioned in a 3' overhang in the Watson strand of the original molecule will be digested and eliminated from the overhang to form a blunt-ended double-stranded molecule. A "C" to "T" conversion positioned near the 5' end of the Crick strand of a molecule having a 3' overhang on the Watson strand may have the 5' overhang digested back and, upon fill-in, be represented in the Watson/Crick strand as T/A. This will likely be propagated in all amplified molecules as T/A. Thus, upon sequencing, "C" to "T" conversion in the double-stranded portion of the original molecule can be detected as errors, as the reads from the original Watson strand will contain T, but reads from the original Crick strand will contain G. In contrast, a "C" to "T" conversion positioned at a 5' overhang in the Watson strand of the original molecule will produce complementary T/A on the Watson/Crick strands, respectively. Thus, conversions of nucleotides in both 5' and 3' overhangs typically do not provide self-evident errors or double-stranded support, e.g., A/T (Watson/Crick) or C/G (Watson/Crick).

Nucleic acid populations can be subject to additional processing such as conversion of single-stranded nucleic acids to double-stranded and/or conversion of RNA to DNA. These forms of nucleic acid can also be linked to adapters and amplified.

With or without prior amplification, nucleic acids subject to blunt-ending as described above, and optionally other nucleic acids in a sample, are sequenced to produce sequenced nucleic acids. A sequenced nucleic acid can refer either to the sequence of a nucleic acid, including sequence reads produced after redundantly sequencing a nucleic acid (e.g., through amplification or re-reading of a single molecule) or a nucleic acid whose sequence has been determined. Sequencing is performed so as to provide sequence data of individual nucleic acid molecules in a sample either directly or indirectly from a consensus sequence of amplification products of an individual nucleic acid molecule in the sample.

In some methods, double-stranded nucleic acids with single-stranded overhangs in a sample after blunt-ending are linked at both ends to adapters including barcodes or tags (attached by ligation or by primer extension), and the sequencing determines nucleic acid sequences as well as barcodes in the adapters. The blunt-ended DNA molecules can be blunt-end ligated with a blunt end of an at least partially double-stranded adapter (e.g., a Y shaped or bell-shaped adapter). Alternatively, blunt ends of sample nucleic acids and adapters can be tailed with complementary nucleotides to facilitate ligation. For instance, the adapters may have a tail, e.g., at least one nucleotide attached or linked onto one of the strands, and the at least one nucleotide is complementary to an overhang introduced on the nucleic acid molecule of interest. The tail on the adapter can be any one or more of the nucleotides, A, T, C, or G.

The sample may be contacted with a sufficient number of adapters that there is a low probability (e.g., <1% or <0.1%) that any two instances of the same nucleic acid receive the same combination of barcodes from the adapters linked at one end or both ends. The use of adapters in this manner permits grouping of sequences with the same start and stop points on a reference nucleic acid and linked to the same combination of barcodes into families of reads generated from the same original molecule. Such a family represents sequences of amplification products of a nucleic acid in the sample before amplification. The sequences of family members can be compiled to derive consensus nucleotide(s) or a complete consensus sequence for a nucleic acid molecule in the original sample, as modified by blunt ending and adapter attachment. In other words, the nucleotide occupying a specified position of a nucleic acid in the sample is determined to be the consensus of nucleotides occupying that corresponding position in family member sequences. A consensus nucleotide can be determined by methods such as voting or confidence score, to name two methods. Families can include sequences of one or both strands of a double-stranded nucleic acid. If members of a family include sequences of both strands from a double-stranded nucleic acid, sequences of one strand are converted to their complement for purposes of compiling all sequences to derive consensus nucleotide(s) or sequences. Some families may include only a single member sequence. In this case, this sequence can be taken as the sequence of a nucleic acid in the sample before amplification. Alternatively, families with only a single member sequence can be eliminated from subsequent analysis.

Nucleotide variations in sequenced nucleic acids can be determined by comparing sequenced nucleic acids with a reference sequence. The reference sequence is often a known sequence, e.g., a known whole or partial genome sequence from an object, whole genome sequence of a human object. The reference sequence can be hG19. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence) and/or the number of sequences in the subset including the reference nucleotide. A variant may be called when supported by the sequenced nucleic acids including the nucleotide variation. For example, if the number of sequenced nucleic acids in the subset including a nucleotide variant exceeds a threshold, then a variant nucleotide can be called at the designated position. The threshold can be a simple number, such as at least 1, 2, 3, 4, 5, 6, 7, 8, 9, or 10 sequenced nucleic acids within the subset including the nucleotide variant or it can be a ratio, such as a least 0.5, 1, 2, 3, 4, 5, 10, 15, or 20% of sequenced nucleic acids within the subset include the nucleotide variant, among other possibilities. The comparison can be repeated for any designated position of interest in the reference sequence. Sometimes a comparison can be performed for designated positions occupying at least 20, 100, 200, or 300 contiguous positions on a reference sequence, e.g., 20-500, or 50-300 contiguous positions. C to T or G to A variations supported by sequenced nucleic acids in the subset with the same confidence as that used to call other variations may nevertheless contain deamination-induced sequencing errors.

Deamination-induced sequencing errors may be inadvertently included in called variant nucleotides unless measures are taken to eliminate them from the called variant nucleotides. Deamination-induced errors can be recognized by either or both of two basic criteria. First, deamination errors are context dependent. Deamination of cytosine to thymine occurs more when the cytosine is flanked by thymine and guanine (i.e., as TCG) than flanked by other nucleotides. Similarly, a variation of guanine to adenine (on the complementary strand) occurs more frequently when the guanine is flanked by C and A as CGA than flanked by other nucleotides. Thus, deamination-induced errors can be called when a C to T or G to A variation occurs in a TCG to TTG or CGA to CAA context respectively. In some methods, about 90% of deamination errors occur in these contexts.

Second, deamination-induced errors depend on the distance between a designated position and an end of a sequenced nucleic acid or, in other words, the number of nucleotides separating these positions. For example, deamination-induced errors occurring in an internal portion of a sequence are likely to be detectable as a "T" in a read from one strand and a "G" in a read from the complementary strand. However, deamination-induced errors occurring proximate to the ends (terminal end) of a nucleic acid being sequenced may not be evident because such errors are introduced by the process of blunt-ended repair, which can result in two perfectly complementary strands. More specifically, sequence reads containing deamination of cytosine to thymine may more frequently occur proximate to the 5' end of a sequenced nucleic acid and deamination of a guanine to an adenine may more frequently occur proximate to the 3' end. Thus, the average distance between a C to T variation arising from deamination at a designated position and the 5' end of sequenced nucleic acids is less than the average distance between the reference nucleotide at the designated position and the 5' end of sequenced nucleic acids. Likewise, the average distance between a G to A variation arising from deamination at a designated position and the 3' end of sequenced nucleic acids is less than the average distance between the reference nucleotide at the designated position and the 3' end of sequenced nucleic acids. The greater the difference in average distances, the greater the probability of a deamination error. Conversely, if a G to A or C to T variation at a designated position represents a real variation rather than a sequencing error there should be no systematic difference that may arise due to random factors between the average distances of these variations and the ends of sequenced nucleic acids compared with those of the reference nucleotide at the designated position.

In certain aspects, provided herein are methods of determining minor allele frequency of a "C" to "T" or a "G" to "A" variant at a designated position in a reference sequence in a population of sequenced polynucleotides mapping to the designated position, wherein minor allele frequency compares a number of sequenced polynucleotides mapping to the designated position comprising the variant ("variant number") to total number of sequenced polynucleotides mapping to the designated position, the method comprising adjusting the variant number of T or A variants at the genomic coordinate for probability of deamination errors, wherein probability of error is a function of distance of the variant from a 5' terminus of a molecule in the case of "T" and from the 3' end of the molecule in case of "A".

Figure 4:
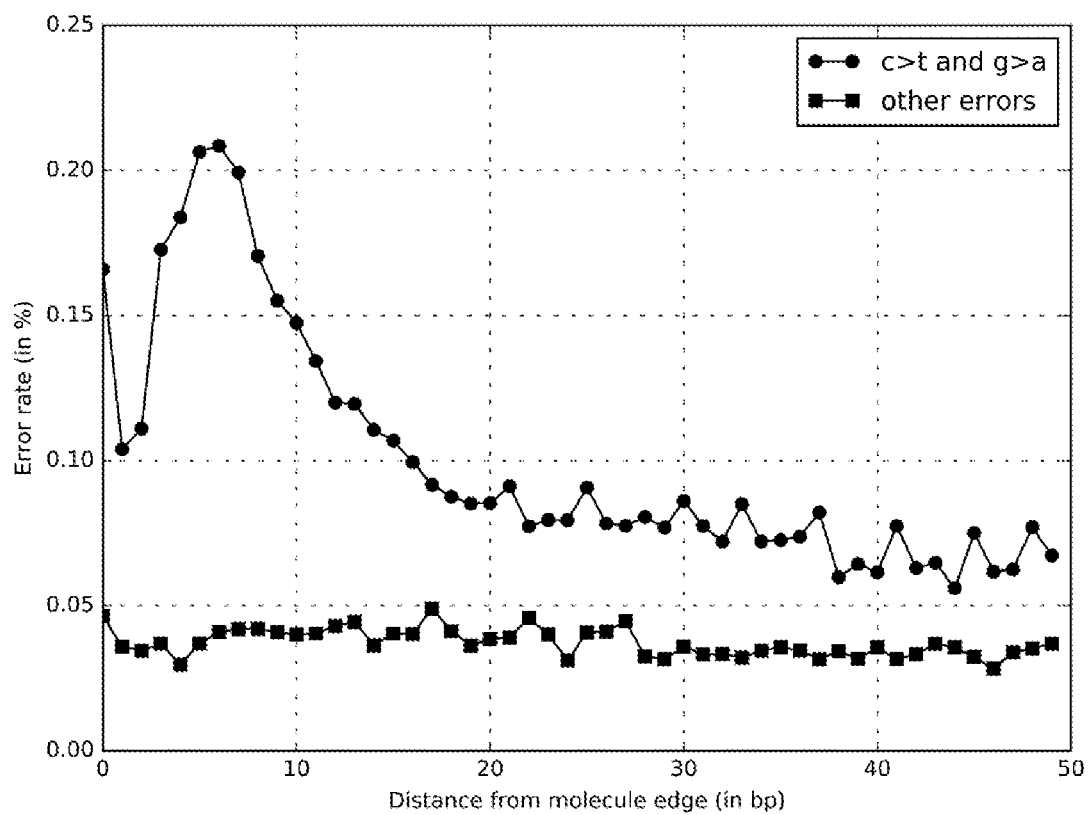
FIG. 4 shows a plot comparing the frequency of errors for C to T and G to A variations and those of other variations with distance from the molecular ends. The error frequency of C to T and G to A variations is much higher close to molecular ends whereas that of other variations is independent of position relative to molecular ends. The points labeled "C>T or G>A" show the average of the rate of C>T errors stratified by the distance measured from 5' end, and the rate of G>A errors stratified by the distance measured from 3' end and the points labeled "other errors" show the average of: the rate of C>A+C>G errors stratified by the distance measured from 5' end, and the rate of G>T+G>C errors stratified by the distance measured from 3' end.

As shown in FIG. 4, the chance of a "T" variant in a molecule resulting from a deamination error is a function of the distance the position of the variant is from the 5' end of a molecule. More specifically, the closer the variant is to the 5' end of the molecule, the more likely that the variant is a C to T transversion. This is because errors are propagated where there is a 5' overhang that is filled in, and shorter overhangs at the 5' end are more likely than longer overhangs. Similarly, G to A variants at the 3' end of the molecule are more likely the closer the position is to the 3' terminus of the molecule, for similar reasons.

In any sample, a statistical determination can be made of C to T variants as a function of distance from the end of the molecule. This function will reach an asymtope at some internal distance in the molecule. The asymptotic amount represents the general deamination rate. This rate may vary from sample to sample.

The relevant proximity to the ends of sequenced nucleic acids in which deamination-induced errors are likely to occur corresponds approximately to the length of single-stranded overhangs in a nucleic acid population being sequenced, but can be slightly longer in the case of a 3' overhang due to digestion beyond the end of the complementary strand and subsequent filling in. The proximity can be defined for example, as less than or equal to 30, 25, 20, 15, 10 or 5 nucleotides from the 3' or 5' end of a sequenced nucleic acid strand ("terminal proximity"). The proximity can be defined the same or differently for the 3' or 5' end.

As previously described, a subset of sequenced nucleic acids is identified including a position corresponding with a designated position of the reference sequence when the respective sequences are maximally aligned. Some of the sequenced nucleic acids within this subset have the designated position occurring within a defined proximity of the 5' end. These sequenced nucleic acids can be referred to as a first fraction of the subset. Some of the sequenced nucleic acids within the subset have the designated position occurring within a defined proximity of the 3' end. These sequenced nucleic acids can be referred to as a second fraction of the subset. A "C" to "T" conversion can then be recognized by its representation in sequenced nucleic acids constituting the first fraction and a "G" to "A" conversion by its representation in sequenced nucleic acids constituting the second fraction. Representation can be defined simply as the number of sequenced nucleic acids present including a C to T or G to A variation at the designated position in the relevant fraction. For example, a C to T deamination error can be called if a certain number, e.g., at least 1, 2, 3, 4, 5 or 6 sequenced nucleic acids of the first fraction including a C to T variation at the designated position. Likewise, a G to A deamination error can be called if a certain number, e.g., at least 1, 2, 3, 4, 5, or 6 sequenced nucleic acids of the second fraction include a G to A variation at the designated position.

Representation can also be defined by the proportion of nucleic acids within the first or second fraction including a C to T or G to A variation at the designated position as compared with the proportion outside the first fraction or second fraction respectively. For example, a deamination error can be called if the representation of a C to T or G to A variation at the designated position with the relevant fraction is at least 25, 30, 40, 50, 60 or 70% of sequenced nucleic acids within the relevant fraction. Overrepresentation can also be defined by the relative proportion of sequenced nucleic acids within the relevant fraction with C to T or G to A variation at the designated position compared with the corresponding proportion of sequenced nucleic acids with the C to T or G to A variation outside the fraction but in the same subset. A higher representation of sequenced nucleic acids within the relevant fraction with the C to T or G to A variation than outside the fraction is an indication the variation is a deamination error. For example, if 50% of sequenced nucleic acids in a first fraction of the subset include a C to T transposition at the designated position, and only 1% of nucleic acids outside the fraction but within the subset (where the designated position is not within the defined proximity of the 5' end), then the C to T transposition is probably a deamination-induced error.

Determining minor allele fraction can comprise calculating a ratio of molecules mapping to a designated position that comprise a particular variant, to total molecules mapping to the designated position. So, for example, if 100 molecules map to the genomic coordinate, and 13 of them comprise the variant, the minor allele frequency can be calculated as 13%. However, if certain variants are considered to be the result of deamination error, these can be discounted from the count. So, for example, if 7 of the 13 variants are designated as errors, the ratio can be calculated as 6/93, or 6.4%. In certain instances, all variants at the designated position may be discounted, for example, if the ratio of variants at the coordinate located at the 5' end of the molecule account for more than 50% of all variants at the coordinate.

Deamination-induced errors can be so categorized based on either context or representation or both. For example, if a C to T or G to A transposition occurs in a context indicated above suggesting a deamination error, then the extent of overrepresentation in the relevant fraction of the subset required to categorize the transposition as a deamination error may be reduced compared with what would be required if the categorization were based on overrepresentation alone.

Whether an apparent variant is called as a deamination error can be based on several factors. The existence of a variant at a locus can be as such when the absolute number of variant molecules is above a certain threshold (e.g., by ratio or by percentage). Also, the existence of a variant can be reported out if the allele fraction (the percent of molecules mapping to a locus bearing the variant) is above a threshold, for example, determined by the expected rate in control samples. When reported out, both the presence of the variant and the minor allele fraction of the variant can be reported out. In reporting out, deamination errors can be treated in any of a number of different ways. In one embodiment, any "T" variants positioned within a predetermined terminal proximity may simply be attributed to error and discounted. In this case, only "T" variants outside of the predetermined terminal proximity are counted as actual variants and subject to reporting requirements. In another method, the fraction of "T" variants positioned within the predetermined terminal proximity to those positioned outside the predetermined terminal proximity is determined. If that amount is above a certain threshold amount, e.g., above 20%, above 30%, above 40%, above 50%, then the error rate is considered high enough that no variant is reported at that position. If the amount is below the threshold level, then the variant is subjected to normal reporting requirements. In another method, if the minor allele fraction is above the expected general error rate then the variant is reported out regardless of the existence of error and may or may not be corrected for error. In another embodiment, at selected positions (which could all be within the proximity zone or could include variants outside the proximity zone) a "T" variant is scored as the probability of the variant being an error, and scores at all positions are added to produce a number to be incorporated in the minor allele fraction. So, for example, the chance of a variant at the first (terminal) 5' nucleotide being a true variant may be 50%. The chance of a variant at the tenth 5' nucleotide might be 75%. The chance of a variant beyond the $20^{th}$ 5' nucleotide might be 95%. If a sample shows one variant at position 1, one at position 10 and one at position 50, these could be scored as 0.5+0.75+0.95=2.2, and counted at 2.2 variants towards the minor allele fraction. Such probabilities can be determined empirically, for example by examining at least 10, at least 50, at least 100 or at least 500 control samples.

When sequencing is performed by identifying families representing amplified copies of a single sequenced nucleic acid in the original sample, typically each family member within a family including families representing both strands of the nucleic acid in the original sample includes the deamination error. If different strands have different nucleotides, the error is self-evident.

The number of designated positions in the reference sequence in which a variant nucleotide is categorized as a deamination error in a particular sample can vary. For example, the number of such designated positions can be at least 1, 2, 3, 4, 5, 6, 7, 8, 9 or 10 among other possibilities.

III. Computer Implementation

The present methods can be computer-implemented, such that any or all of the steps described in the specification or appended claims other than wet chemistry steps can be performed in a suitable programmed computer. The computer can be a mainframe, personal computer, tablet, smart phone, cloud, online data storage, remote data storage, or the like. The computer can be operated in one or more locations.

A computer program for analyzing a nucleic acid population can include codes for performing any of the steps other than wet chemistry steps described in the specification or in the appended claims; for example codes for determining sequences of the double-stranded blunt-ended nucleic acids to provide sequenced nucleic acids; code for identifying a subset of sequenced nucleic acids including the designated position and identifying the number of sequenced nucleic acids in the subset in which the designated position is occupied by a variant nucleotide at each designated position in a reference sequence; and code for calling presence of a variant nucleotide at each designated position at which the number of sequenced nucleic acids in the subset with the variation meets a threshold, except that presence of a variant nucleotide at a designated position is not called if: (i) the variant is a C to T or G to A variation compared with the reference nucleotide; and (ii) the variant nucleotide is categorized as a deamination error based on: (1) nucleotide context around the designated position and/or (2) distance of the C to T variation at the designated position from the 5'-end in sequenced nucleic acids in the subset or distance of the G to A variation at the designated position from the 3'-end in sequenced nucleic acids in the subset. The computer program can also include codes for receiving sequence data from a database or sequencing apparatus and outputting calculated data, such as variant nucleotides or deamination-induced sequencing errors to a display or printer.

The present methods can be implemented in a system (e.g., a data processing system) for analyzing a nucleic acid population. The system can also include a processor, a system bus, a main memory and optionally an auxiliary memory coupled to one another to perform one or more of the steps described in the specification or appended claims, such as the following: determining sequences of the double-stranded blunt-ended nucleic acids to provide sequenced nucleic acids; identifying a subset of sequenced nucleic acids including the designated position and identifying the number of sequenced nucleic acids in the subset in which the designated position is occupied by a variant nucleotide at each designated position in a reference sequence; and calling presence of a variant nucleotide at each designated position at which the number of sequenced nucleic acids in the subset with the variation meets a threshold, except that presence of a variant nucleotide at a designated position is not called if: (i) the variant is a C to T or G to A variation compared with the reference nucleotide; and (ii) the variant nucleotide is categorized as a deamination error based on: (1) nucleotide context around the designated position and/or (2) distance of the C to T variation at the designated position from the 5'-end in sequenced nucleic acids in the subset or distance of the G to A variation at the designated position from the 3'-end in sequenced nucleic acids in the subset. The system can also include a display or printer for outputting results, such as variant nucleotides and deamination-induced errors, a keyboard and/or pointer for providing user input, such as setting thresholds or defined proximities, among other accessories. The system can also include a sequencing apparatus coupled to the memory to provide raw sequencing data.

Various steps of the present methods can utilize information and/or programs and generate results that are stored on computer-readable media (e.g., hard drive, auxiliary memory, external memory, server; database, portable memory device (e.g., CD-R, DVD, ZIP disk, flash memory cards), and the like. For example, information used for and results generated by the methods that can be stored on computer-readable media include references sequences, thresholds or defined proximities for nucleotide variant or deamination-induced error calls, raw sequencing data, sequenced nucleic acids, variant nucleotides and their associations with disease, and deamination-induced errors.

The present disclosure also includes an article of manufacture for analyzing a nucleic acid population that includes a machine-readable medium containing one or more programs which when executed implement the steps of the present methods.

The disclosure can be implemented in hardware and/or software. For example, different aspects of the disclosure can be implemented in either client-side logic or server-side logic. The disclosure or components thereof can be embodied in a fixed media program component containing logic instructions and/or data that when loaded into an appropriately configured computing device cause that device to perform according to the disclosure. A fixed media containing logic instructions can be delivered to a viewer on a fixed media for physically loading into a viewer's computer or a fixed media containing logic instructions may reside on a remote server that a viewer accesses through a communication medium to download a program component.

Figure 5:
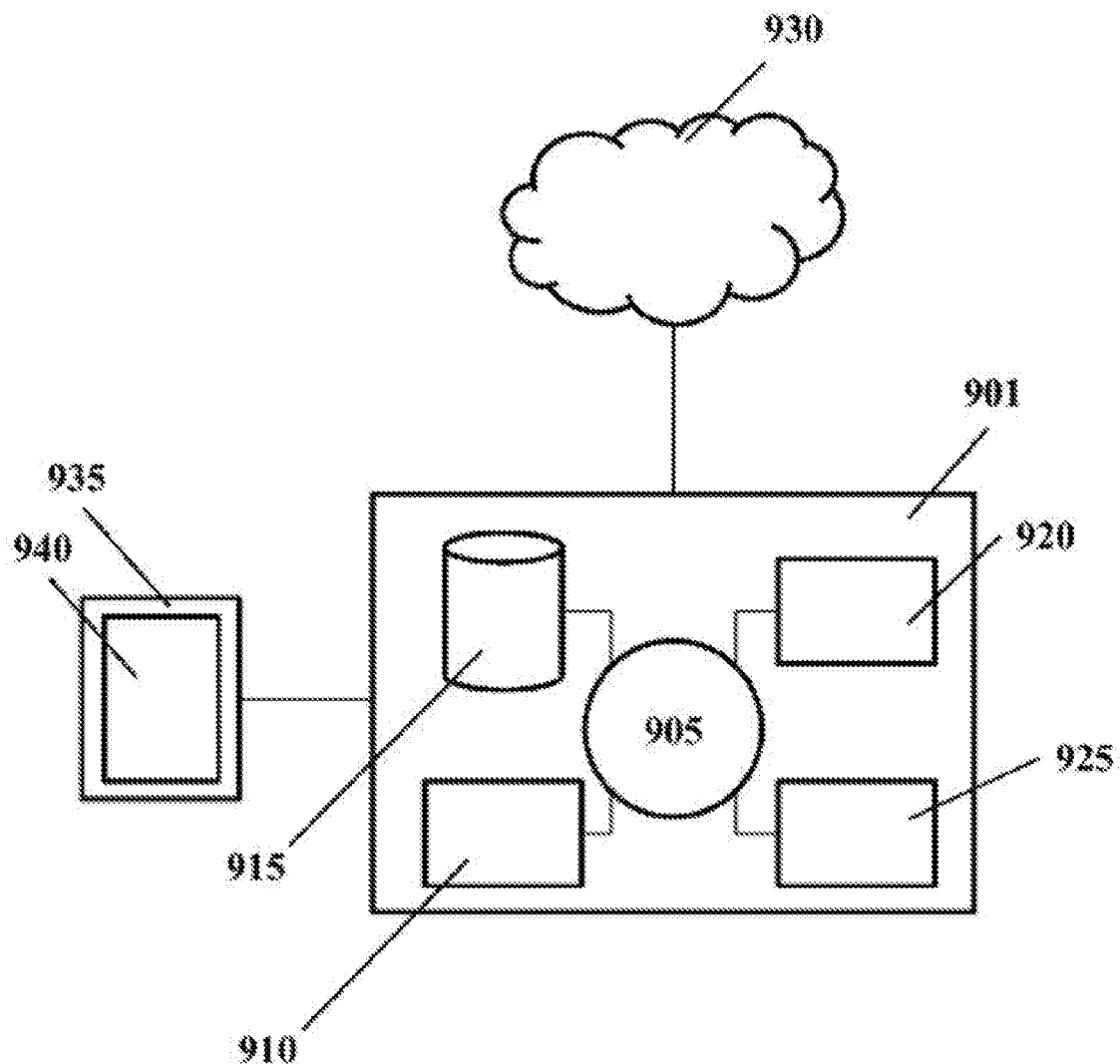
FIG. 5 shows a computer system.

The present disclosure provides computer control systems that are programmed to implement methods of the disclosure. FIG. 5 shows a computer system 901 that is programmed or otherwise configured to implement methods of the present disclosure. The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905

Through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include a local area network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented byway of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processer adapted to execute the code, or can be compiled during runtime. The code can be supplied in a programming language that can be selected to enable the code to execute in a precompiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk.

"Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "Storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, a report. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905.

IV. General Features of the Methods

1. Samples

A sample can be any biological sample isolated from a subject. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine. Samples are preferably body fluids, particularly blood and fractions thereof, and urine. Such samples include nucleic acids shed from tumors. The nucleic acids can include DNA and RNA and can be in double- and/or single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a body fluid for analysis is plasma or serum containing cell-free nucleic acids, e.g., cell-free DNA (cfDNA).

The volume of plasma can depend on the desired read depth for sequenced regions. Exemplary volumes are 0.4-40 ml, 5-20 ml, 10-20 ml. For example, the volume can be 0.5 ml, 1 ml, 5 ml, 10 ml, 20 ml, 30 ml, or 40 ml. A volume of sampled plasma may be 5 to 20 ml.

The sample can comprise various amounts of nucleic acid that contains genome equivalents. For example, a sample of about 30 ng DNA can contain about 10,000 ($10^4$) haploid human genome equivalents and, in the case of cfDNA, about 200 billion ($2 \times 10^4$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources, e.g., from cells and cell free. A sample can comprise nucleic acids carrying mutations. For example, a sample can comprise DNA carrying germline mutations and/or somatic mutations. A sample can comprise DNA carrying cancer-associated mutations (e.g., cancer-associated somatic mutations).

Exemplary amounts of cell free nucleic acids in a sample before amplification range from about 1 fg to about 1 μg, e.g., 1 pg to 200 ng, 1 ng to 100 ng, 10 ng to 1000 ng. For example, the amount can be up to about 600 ng, up to about 500 ng, up to about 400 ng, up to about 300 ng, up to about 200 ng, up to about 100 ng, up to about 50 ng, or up to about 20 ng of cell-free nucleic acid molecules. The amount can be at least 1 fg, at least 10 fg, at least 100 fg, at least 1 pg, at least 10 pg, at least 100 pg, at least 1 ng, at least 10 ng, at least 100 ng, at least 150 ng, or at least 200 ng of cell-free nucleic acid molecules. The amount can be up to 1 femtogram (fg), 10 fg, 100 fg, 1 picogram (pg), 10 pg, 100 pg, 1 ng, 10 ng, 100 ng, 150 ng, or 200 ng of cell-free nucleic acid molecules. The method can comprise obtaining 1 femtogram (fg) to 200 ng.

A cell-free nucleic acid sample refers to a sample containing cell-free nucleic acids. Cell-free nucleic acids are nucleic acids not contained within or otherwise bound to a cell or in other words nucleic acids remaining in a sample after removing intact cells. Cell-free nucleic acids can be referred to all non-encapsulated nucleic acid sourced from a bodily fluid (e.g., blood, urine, CSF, etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), or fragments of any of these. Cell-free nucleic acids can be double-stranded, single-stranded, or a hybrid thereof. A cell-free nucleic acid can be released into bodily fluid through secretion or cell death processes, e.g., cellular necrosis and apoptosis. Some cell-free nucleic acids are released into bodily fluid from cancer cells e.g., circulating tumor DNA (ctDNA). Others are released from healthy cells. ctDNA can be non-encapsulated tumor-derived fragmented DNA. Cell-free fetal DNA (cffDNA) is fetal DNA circulating freely in the maternal blood stream.

A cell-free nucleic acid or proteins associated with it can have one or more epigenetic modifications, for example, a cell-free nucleic acid can be acetylated, 5-methylated, ubiquitylated, phosphorylated, sumoylated, ribosylated, and/or citrullinated.

Cell-free nucleic acids have an exemplary size distribution of about 100-500 nucleotides, with molecules of 110 to about 230 nucleotides representing about 90% of molecules, with a mode of about 168 nucleotides in humans and a second minor peak in a range between 240 to 440 nucleotides. Cell-free nucleic acids can be about 160 to about 180 nucleotides, or about 320 to about 360 nucleotides, or about 440 to about 480 nucleotides.

Cell-free nucleic acids can be isolated from bodily fluids through a partitioning step in which cell-free nucleic acids, as found in solution, are separated from intact cells and other non-soluble components of the bodily fluid. Partitioning may include techniques such as centrifugation or filtration. Alternatively cells in bodily fluids can be lysed and cell-free and cellular nucleic acids processed together. Generally, after addition of buffers and wash steps, cell-free nucleic acids can be precipitated with an alcohol. Further clean up steps may be used such as silica based columns to remove contaminants or salts. Non-specific bulk carrier nucleic acids, for example, may be added throughout the reaction to optimize certain aspects of the procedure such as yield.

After such processing, samples can include various forms of nucleic acid including double-stranded DNA, single stranded DNA and single stranded RNA. Optionally, single stranded DNA and RNA can be converted to double-stranded forms so they are included in subsequent processing and analysis steps.

2. Amplification

Sample nucleic acids flanked by adapters can be amplified by PCR and other amplification methods typically primed from primers binding to primer binding sites in adapters flanking a DNA molecule to be amplified. Amplification methods can involve cycles of extension, denaturation and annealing resulting from thermocycling or can be isothermal as in transcription mediated amplification. Other amplification methods include the ligase chain reaction, strand displacement amplification, nucleic acid sequence based amplification, and self-sustained sequence based replication.

One or more amplifications can be applied to introduce barcodes to a nucleic acid molecule using conventional nucleic acid amplification methods. The amplification can be conducted in one or more reaction mixtures. Molecule tags and sample indexes/tags can be introduced simultaneously, or in any sequential order. Molecule tags and sample indexes/tags can be introduced prior to and/or after sequence capturing. In some cases, only the molecule tags are introduced prior to probe capturing while the sample indexes/tags are introduced after sequence capturing. In some cases, both the molecule tags and the sample indexes/tags are introduced prior to probe capturing. In some cases, the sample indexes/tags are introduced after sequence capturing. Usually, sequence capturing involves introducing a single-stranded nucleic acid molecule complementary to a targeted sequence, e.g., a coding sequence of a genomic region and mutation of such region is associated with a cancer type. Typically, the amplifications generate a plurality of non-uniquely or uniquely tagged nucleic acid amplicons with molecule tags and sample indexes/tags at a size ranging from 200 nt to 700 nt, 250 nt to 350 nt, or 320 nt to 550 nt. In some embodiments, the amplicons have a size of about 300 nt. In some embodiments, the amplicons have a size of about 500 nt.

3. Barcodes

Barcodes can be incorporated into or otherwise joined to adapters by chemical synthesis, ligation, overlap extension PCR among other methods. Generally, assignment of unique or non-unique barcodes in reactions follows methods and systems described by US patent applications 20010053519, 20110160078, and U.S. Pat. Nos. 6,582,908 and 7,537,898 and 9,598,731.

Tags can be linked to sample nucleic acids randomly or non-randomly. In some cases, they are introduced at an expected ratio of identifiers (e.g., a combination of barcodes) to microwells. The collection of barcodes can be unique, e.g., all the barcodes have the same nucleotide sequence. The collection of barcodes can be non-unique, e.g., some of the barcodes have the same nucleotide sequence, and some of the barcodes have different nucleotide sequence. For example, the identifiers may be loaded so that more than 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 identifiers are loaded per genome sample. In some cases, the identifiers may be loaded so that less than 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 identifiers are loaded per genome sample. In some cases, the average number of identifiers loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 identifiers per genome sample.

A preferred format uses 20-50 different tags, ligated to both ends of a target molecule creating 20-50×20-50 tags, e.g., 400-2500 tags. Such numbers of tags are sufficient that different molecules having the same start and stop points have a high probability (e.g., at least 94%, 99.5%, 99.99%, 99.999%) of receiving different combinations of tags.

In some cases, identifiers may be predetermined or random or semi-random sequence oligonucleotides. In other cases, a plurality of barcodes may be used such that barcodes are not necessarily unique to one another in the plurality. In this example, barcodes may be attached (e.g., by ligation or PCR amplification) to individual molecules such that the combination of the barcode and the sequence it may be attached to creates a unique sequence that may be individually tracked. As described herein, detection of non-uniquely tagged barcodes in combination with sequence data of beginning (start) and end (stop) portions of sequence reads may allow assignment of a unique identity to a particular molecule. The length, or number of base pairs, of an individual sequence read may also be used to assign a unique identity to such a molecule. As described herein, fragments from a single strand of nucleic acid having been assigned a unique identity, may thereby permit subsequent identification of fragments from the parent strand, and/or a complementary strand.

4. Sequencing

Sample nucleic acids flanked by adapters with or without prior amplification can be subject to sequencing. Sequencing methods include, for example, Sanger sequencing, high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, ION TORRENT™, Oxford Nanopore, Roche Genia, Maxim-Gilbert sequencing, primer walking, sequencing using PacBio, SOLiD, ION TORRENT™, or Nanopore platforms. Sequencing reactions can be performed in a variety of sample processing units, which may be multiple lanes, multiple channels, multiple wells, or other means of processing multiple sample sets substantially simultaneously. Sample processing unit can also include multiple sample chambers to enable processing of multiple runs simultaneously.

The sequencing reactions can be performed on one or more fragments types known to contain markers of cancer of other disease. The sequencing reactions can also be performed on any nucleic acid fragments present in the sample. The sequence reactions may provide for sequence coverage of the genome of at least 5%, 10%, 15%, 20%, 25%, 30%, 40%, 50%, 60%, 70%, 80%, 90%, 95%, 99%, 99.9% or 100%. In other cases, sequence coverage of the genome may be less than 5%, 10%, 15%, 20%, 25%, 30%, 40%, 50%, 60%, 70%, 80%, 90%, 95%, 99%, 99.9% or 100%.

Simultaneous sequencing reactions may be performed using multiplex sequencing.

In some cases, cell free polynucleotides may be sequenced with at least 1000, 2000, 3000, 4000, 5000, 6000, 7000, 8000, 9000, 10000, 50000, 100,000 sequencing reactions. In other cases, cell free polynucleotides may be sequenced with less than 1000, 2000, 3000, 4000, 5000, 6000, 7000, 8000, 9000, 10000, 50000, 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, 100,000 sequencing reactions. In other cases, data analysis may be performed on less than 1000, 2000, 3000, 4000, 5000, 6000, 7000, 8000, 9000, 10000, 50000, 100,000 sequencing reactions. An exemplary read depth is 1000-50000 reads per locus (base).

5. Analysis

The present methods can be used to diagnose presence of conditions, particularly cancer, in a subject, to characterize conditions (e.g., staging cancer or determining heterogeneity of a cancer), monitor response to treatment of a condition, effect prognosis risk of developing a condition or subsequent course of a condition.

Various cancers may be detected using the present methods. Cancers cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as rare mutations. This phenomenon may be used to detect the presence or absence of cancers individuals using the methods and systems described herein.

The types and number of cancers that may be detected may include blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

Cancers can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers progress, becoming more aggressive and genetically unstable. Other cancers may remain benign, inactive or dormant. The system and methods of this disclosure may be useful in determining disease progression.

The present analysis is also useful in determining the efficacy of a particular treatment option. Successful treatment options may increase the amount of copy number variation or rare mutations detected in a subject's blood if the treatment is successful as more cancers may die and shed DNA. In other examples, this may not occur. In another example, perhaps certain treatment options may be correlated with genetic profiles of cancers overtime. This correlation may be useful in selecting a therapy. Additionally, if a cancer is observed to be in remission after treatment, the present methods can be used to monitor residual disease or recurrence of disease.

The present methods can also be used for detecting genetic variations in conditions other than cancer. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing. Copy number variation or even rare mutation detection may be used to determine how a population of pathogens are changing during the course of infection. This may be particularly important during chronic infections, such as HIV/AIDs or Hepatitis infections, whereby viruses may change life cycle state and/or mutate into more virulent forms during the course of infection. The present methods may be used to determine or profile rejection activities of the host body, as immune cells attempt to destroy transplanted tissue to monitor the status of transplanted tissue as well as altering the course of treatment or prevention of rejection.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and rare mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation and rare mutation analyses alone or in combination.

The present methods can be used to diagnose, prognose, monitor or observe cancers or other diseases of fetal origin. That is, these methodologies may be employed in a pregnant subject to diagnose, prognose, monitor or observe cancers or other diseases in a unborn subject whose DNA and other polynucleotides may co-circulate with maternal molecules.

6. Treatment

The number and types of variant nucleotides in a sample can provide an indication of the amenability of the subject providing the sample to treatment, i.e., therapeutic intervention. For example, presence of a high number of variants nucleotides is a positive indicator for immunotherapy because the presence of such mutation is associated with neoepitopes forming targets for immunotherapy. Immunotherapy can include use of an antibody against any of PD-1, PD-2, PD-L1, PD-L2, CTLA-40, OX40, B7.1, B7He, LAG3, CD137, KIR, CCR5, CD27, or CD40 among other treatments. Other exemplary agents for immunotherapy include proinflammatory cytokines, such as IL-1β, IL-6, and TNF-α. Other exemplary agents are T-cells activated against a tumor, such as by expressing of a chimeric antigen targeting a tumor antigen from the T-cell. Immunotherapy stimulates the immune system to attack tumor antigens distinguished from wildtype counterparts by the presence of mutation(s).

Other variant nucleotides provide targets for existing drugs or indicate resistance to such drugs. Eliminating false positive due to deamination-induced sequencing errors increases the accuracy with which the number and types of variant nucleotides can be determined. Thus, subjects analyzed by the present methods can thereafter be subject to differential treatment regimes depending on the nucleotide variants discovered. Thus, for example, a greater proportion of subjects whose number of determined variant nucleotides is at or exceeds a threshold can receive immunotherapy than subjects with number of determined variant nucleotides is below the threshold.

Nucleotide variations in sequenced nucleic acids can be determined by comparing sequenced nucleic acids with a reference sequence. The reference sequence is often a known sequence, e.g., a known whole or partial genome sequence from an object, whole genome sequence of a human object. The reference sequence can be hG19. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence). If the number of sequenced nucleic acids in the subset including a nucleotide variant exceeds a threshold, then a variant nucleotide can be called at the designated position. The threshold can be a simple number, such as at least 1, 2, 3, 4, 5, 6, 7, 8, 9, or 10 sequenced nucleic acid within the subset including the nucleotide variant or it can be a ratio, such as a least 0.5, 1, 2, 3, 4, 5, 10, 15, or 20 of sequenced nucleic acids within the subset include the nucleotide variant, among other possibilities.

The comparison can be repeated for any designated position of interest in the reference sequence. Sometimes a comparison can be performed for designated positions occupying at least 20, 100, 200, or 300 contiguous positions on a reference sequence, e.g., 20-500, or 50-300 contiguous positions.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

Example 1

Figure 6:
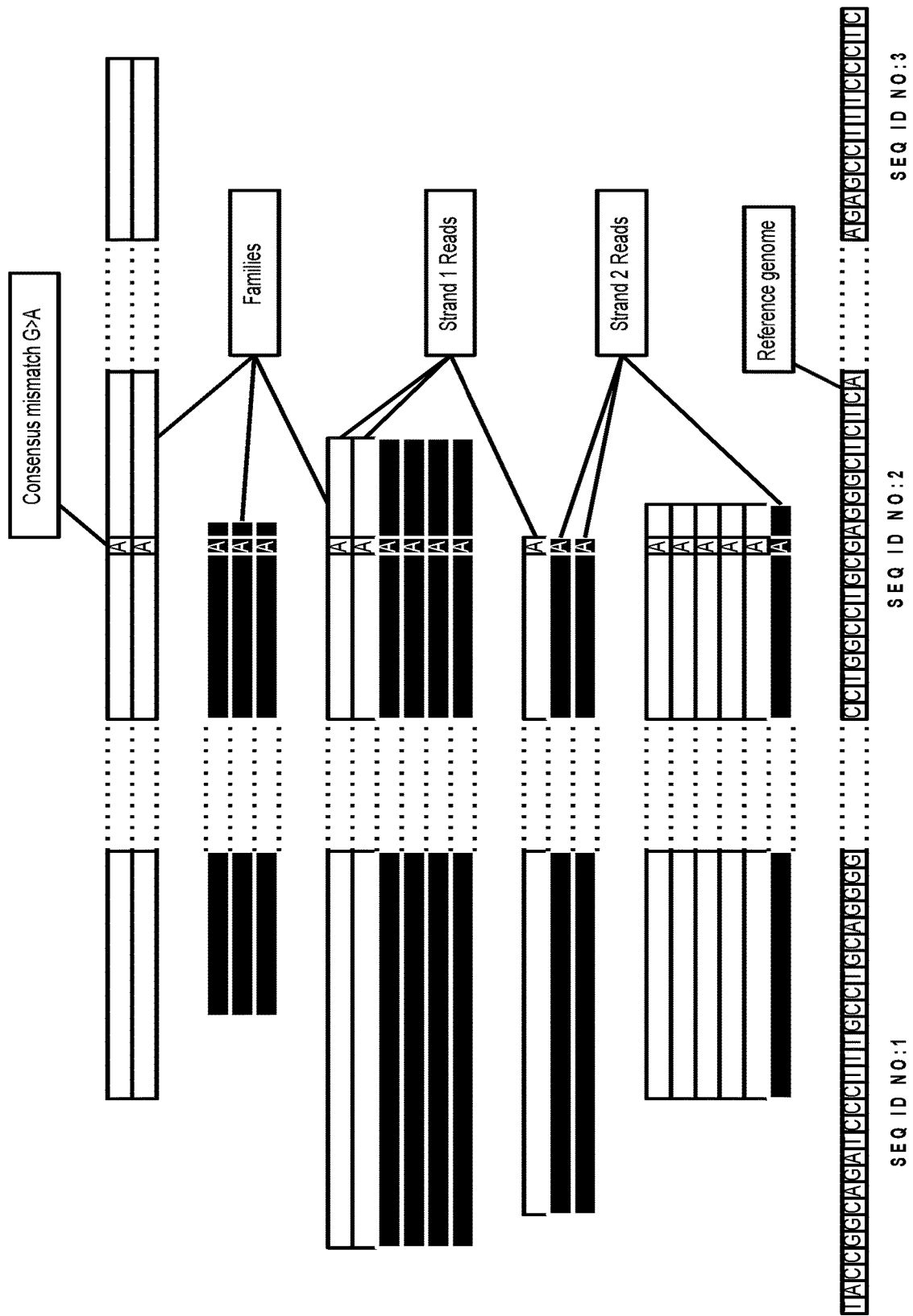
FIG. 6 shows five sequencing families including a G to A substitution classified as a deamination error. The left-hand segment of reference genome sequence is SEQ ID NO:1, the middle segment of reference genome sequence is SEQ ID NO:2, and the right-hand segment of reference genome sequence is SEQ ID NO:3.

FIG. 6 shows families of sequencing reads of cell free DNA. The sequencing reads map to various segment of an ALK gene (CD246) on human chromosome 2. The reference sequence of the relevant region of the ALK gene is shown at the bottom of the figure (the gap in the sequence represents additional nucleotides not shown for conciseness of the figure). The figure shows five families of sequencing reads having 2, 3, 6, 3 and 6 reads respectively from top to bottom. Reads from one orientation are shown in black and reads from the other orientation are shown in white. Each of the families shows a G to A mismatch in each read of the family. Viewed in isolation, these families of sequencing reads provide sufficient evidence to call a G to A mutation. However, this picture changes when the position of the G to A mutation is considered relative to the 3' end of the sequence reads as follows:

(1) Family 1: first strand: 2 reads, second strand: no reads, G>A mutation located 70 bases off the 3' end
(2) Family 2: first strand: no reads, second strand: 3 reads, G>A mutation located 2 bases off the 3' end
(3) Family 3: first strand: 2 reads, second strand: 4 reads, G>A mutation located 6 bases off the 3' end
(4) Family 4: first strand: 1 read, second strand: 2 reads, G>A mutation located 1 bases off the 3' end
(5) Family 5: first strand: 5 reads, second strand: 1 read, G>A mutation located 3 bases off the 3' end In four of the five families (80%) in which a G to A substitution is seen, the substitution occurs within 20 bases of the 3' end of the sequencing read. The figure of 80% exceeds 50% of families with a G to A substitution having the substitution within 20 bases of the 3' end of a sequencing read. Therefore, the substitution is classified as a deamination induced error of no functional significance rather than a bona fide mutation (which may have implications with respect to cancer diagnosis or prognosis).

Example 2

Figure 7:
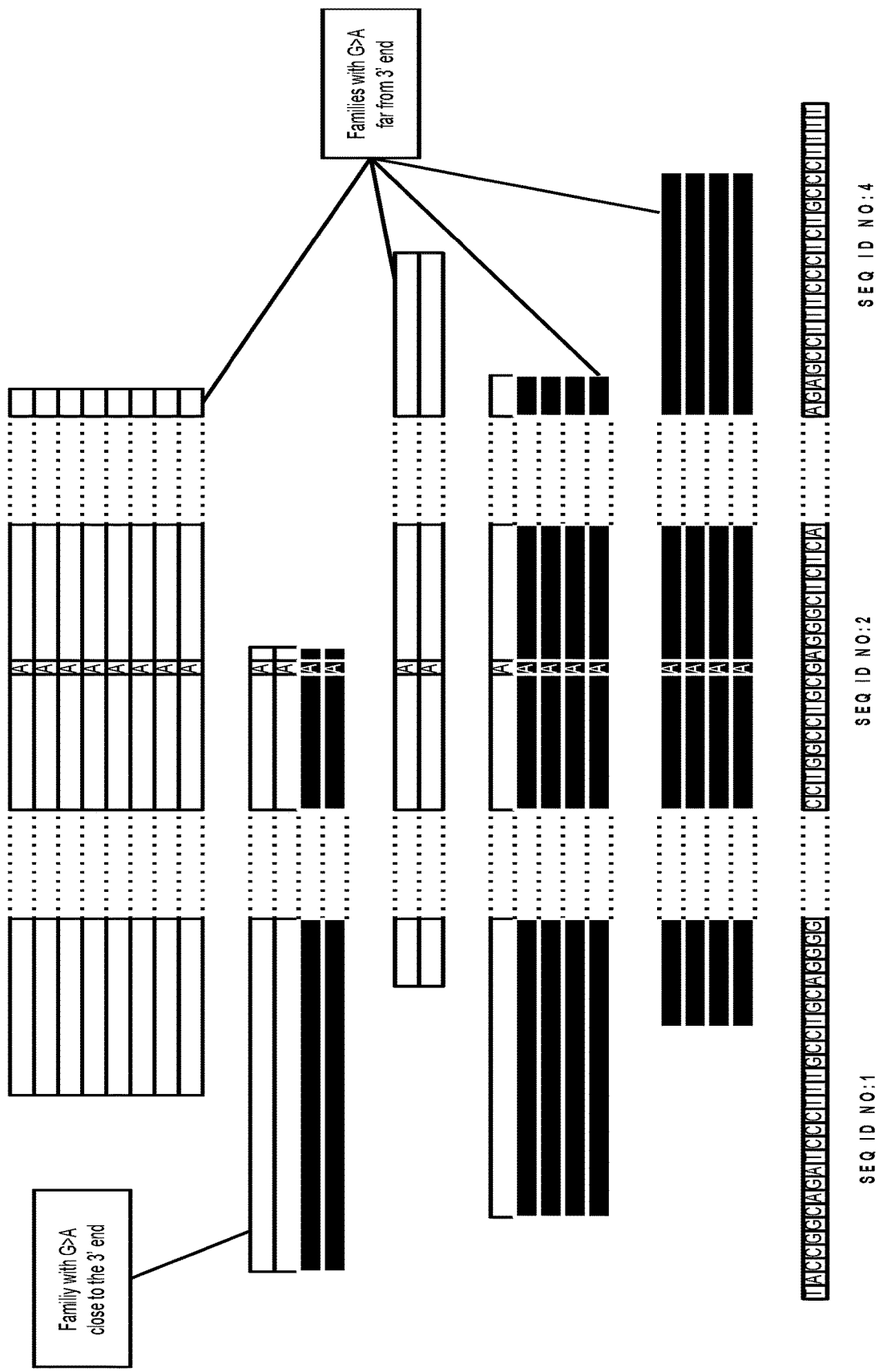
FIG. 7 shows five sequencing families including a G to A substitution classified as a bona fide mutation. The left-hand segment of reference genome sequence is SEQ ID NO:1, the middle segment of reference genome sequence is SEQ ID NO:2, and the right-hand segment of reference genome sequence is SEQ ID NO:4.

FIG. 7 is presented in similar format to FIG. 6 showing sequencing reads from five families with 8, 4, 2, 5 and 4 members respectively. Again each of the five families has an apparent G to A substitution in each of its reads. However, in this case, the relative positions of the substitution to the 3' end of sequencing reads is different as shown below:

(1) Family 1: first strand: 8 reads, second strand: no reads, G>A mutation located 62 bases off the 3' end
(2) Family 2: first strand: 2 reads, second strand: 2 reads, G>A mutation located 2 bases off the 3' end
(3) Family 3: first strand: 2 reads, second strand: no reads, G>A mutation located 72 bases off the 3' end
(4) Family 4: first strand: 1 read, second strand: 4 reads, G>A mutation located 63 bases off the 3' end
(5) Family 5: first strand: no reads, second strand: 4 reads, G>A mutation located 79 bases off the 3' end In this case only one of the five families (20%) has the apparent G to A substitution within 20 bases of the 3' end of its sequencing reads. 20% does not exceed the 50% cut off for classifying the mutation as a deamination error. Therefore, the apparent G to A substitution is classified as a bona fide mutation.

What is claimed is:

1. A method for identifying variant nucleotides in a population of cell-free nucleic acids comprising:
   (a) contacting a population of cell-free nucleic acids comprising double-stranded molecules with single-stranded overhangs at one or both ends with a protein having 5'-3' polymerase activity and a 3'-5' exonuclease activity, wherein the protein digests 3' overhangs and fills in 5' overhangs with complementary nucleic acids, to generate double-stranded blunt-ended nucleic acids, at one or both ends;
   (b) determining sequences of a plurality of the double-stranded blunt-ended nucleic acids to provide sequenced nucleic acids;
   (c) for each designated position in a reference sequence,
      (i) identifying a subset of sequenced nucleic acids including the designated position, and
      (ii) identifying sequenced nucleic acids in the subset in which the designated position is occupied by a variant nucleotide; and
   (d) calling presence of a variant nucleotide at each designated position for which the sequenced nucleic acids in step (c)(ii) support the call, except that presence of a variant nucleotide at a designated position is not called if:
      (i) the variant is a C to T or G to A variation compared with the reference nucleotide; and
      (ii) the variant nucleotide is classified as a deamination error based on:
         (1) nucleotide context around the designated position and/or
         (2) distance of the C to T variation at the designated position from the 5'-end in sequenced nucleic acids in the subset or distance of the G to A variation at the designated position from the 3'-end in sequenced nucleic acids in the subset;
      wherein at least one variant nucleotide which would otherwise have been called in step (d) is not called due to conditions (i) and (ii) being determined to have been met.

2. The method of claim 1, wherein step (c)(ii) identifies the number of nucleic acids in the subset in which the designated position is occupied by a variant nucleotide and presence of a variant nucleotide at each designated position is called when the number of sequenced nucleic acids in the subset with the variation meets a threshold except as specified in steps (d)(i) and (ii).

3. The method of claim 2, wherein the threshold is that the variation is present in at least 1% of the sequenced nucleic acids in the subset.

4. The method of claim 1, wherein the variant nucleotide is classified as a deamination error based on the representation of the C to T variation at the designated position within a defined proximity of the 5'-end in sequenced nucleic acids in the subset or representation of the G to A variation at the designated position within a defined proximity of the 3'-end in sequenced nucleic acids in the subset.

5. The method of claim 4, wherein the defined proximity to the 5' end is defined as being within 20 nucleotides or within a fewer number of nucleotides to the 5' end and the defined proximity to the 3' end is defined as being within 20 nucleotides or within a fewer number of nucleotides to the 3' end.

6. The method of claim 5, wherein the defined proximity to the 5' end is defined as being within 20 nucleotides to the 5' end and the defined proximity to the 3' end is defined as being within 20 nucleotides to the 3' end.

7. The method of claim 1, wherein step (c)(ii) further comprises identifying the number of sequenced nucleic acids in the subset in which the designated position is occupied by a reference nucleotide.

8. The method of claim 1, wherein step (b) comprises determining sequences of both strands of the double-stranded blunt-ended nucleic acid.

9. The method of claim 8, wherein step (c) is performed for at least one designated position wherein the sequenced nucleic acids in the subset with the variation include sequences of both strands of the double-stranded blunt-ended sequenced nucleic acid.

10. The method of claim 1, wherein step (b) comprises determining sequences from both ends of a double-standed blunt-ended nucleic acid.

11. The method of claim 1, wherein the cell-free nucleic acids are obtained from a body fluid of a subject having a cancer or having signs or symptoms consistent with having a cancer.

12. The method of claim 1, wherein the C to T variation at the designated position is classified as a deamination error if its representation is at least 50% in a first fraction of the subset in which the designated position is within a defined proximity of the 5' end or the G to A variation at the designated position is classified as a deamination error if its representation is at least 50% in a second fraction of the subset in which the designated position is within a defined proximity of the 3' end.

13. The method of claim 1, wherein the C to T variation at the designated position is classified as a deamination error based on the variation having at least twice the representation in a first fraction of the subset in which the designated position is within a defined proximity of the 5' end than in other sequenced nucleic acid in the subset, or the G to A variation at the designated position is classified as a deamination error based on the variation having at least twice the representation in a second fraction of the subset in which the designated position is within a defined proximity to the 3' end than in other sequenced nucleic acids in the subset.

14. The method of claim 1, wherein the C to T or G to A variation is classified as a deamination error at least based on the surrounding context being TCG to TTG or CGA to CAA.

15. The method of claim 1, wherein the protein is Klenow.

16. The method of claim 1, wherein steps (c) and (d) are performed in a computer-operated system programmed to carry out these steps.

17. The method of claim 1, wherein the reference sequence is a sequence of a human genome.

18. The method of claim 1, wherein at least one of the variant nucleotides called is known to be associated with a cancer.

19. The method of claim 1, wherein variant nucleotides classified as deamination errors are at least 1% of the called variant nucleotides.

20. The method of claim 1, wherein the presence of a variant is not called if at least 5 variant nucleotides at a designated position are classified as deamination errors.

21. The method of claim 1, wherein the variant nucleotide is classified as a deamination error based on the average distance of the C to T variation at the designated position being less than the average distance of the reference nucleotide at the designated position from the 5'-end of sequenced nucleic acids in the subset or the G to A variation at the designated position being less than the average distance of the reference nucleotide at the designated position from the 3'-end of sequenced nucleic acids in the subset.

22. The method of claim 1, wherein the variant nucleotide is a single nucleotide variant (SNV).

23. The method of claim 1, wherein the population of cell-free nucleic acids are non-encapsulated nucleic acids source from a bodily fluid.

24. A method identifying variant nucleotides in a cell-free nucleic acid, comprising:
(a) contacting a cell-free double-stranded nucleic acid with single-stranded overhangs with a protein having 5'-3' polymerase activity and a 3'-5' exonuclease activity thereby producing a double-stranded blunt-ended nucleic acid;
(b) determining a sequence of the double-stranded blunt-ended nucleic acid;
(c) comparing the determined sequence to a reference sequence, wherein the determined sequence includes at least one C to T variation in at least one designated position within 20 nucleotides or fewer of the 5' end of the determined sequence or at least one G to A variation within 20 nucleotides or fewer of the 3' end of the determined sequence; and
(d) calling a sequence for the nucleic acid as the determined sequence except in at least one of the positions in which a C to T variation is present within 20 nucleotides or fewer of the 5' end of the determined sequence or a G to A variation within 20 nucleotides or fewer of the 3' end of the determined sequence, where the nucleotide occupying the reference sequence is called at the designated position.

25. The method of claim 24, wherein the C to T or G to A variation occurs in a surrounding context of TCG to TTG or CGA to CAA.

26. A method identifying variant nucleotides in a population of cell-free nucleic acids comprising:
(a) contacting a population of nucleic acids of overlapping sequences at least one of which is a double-stranded molecule with single-stranded overhangs at one or both ends with a protein having 5'-3' polymerase activity and a 3'-5' exonuclease activity, wherein the protein digests 3' overhangs and fills in 5' overhangs to generate double-stranded blunt-ended nucleic acids;
(b) linking the double-stranded blunt-ended nucleic acids to adapters comprising molecular barcodes;
(c) amplifying the nucleic acids primed from primer molecules binding to the adapters;
(d) determining sequences of amplified nucleic acid molecules and classifying the sequences of the amplified nucleic acid molecules into families, the members of a family having the same start and stop points on the nucleic acid and the same barcodes, and determining consensus sequences for the families from the sequences of their respective members;
(e) for each designated position in a reference sequence determining a subset of families having a consensus sequence including the designated position and identifying consensus sequences in the subset in which the designated position is occupied by a variant nucleotide; and
(f) calling presence of a variant nucleotide at designated position at which the consensus sequences in the subset with the variant nucleotide support the call except that presence of a variant nucleotide at a designated position is not called if:
(i) the variant nucleotide is a C to T or G to A variation compared with the reference nucleotide; and
(ii) the variant nucleotide is classified as a deamination error based on:
(1) nucleotide context around the designated position and/or
(2) distance of the C to T variation at the designated position in consensus sequences in the subset from the 5' end or distance of the G to A variation at the designated position in consensus sequences from the 3' end; wherein at least one variant nucleotide which would otherwise have been called in step (f) is not called due to conditions (i) and (ii) being determined to have been met.

27. The method of claim 26, wherein step (e) identifies the number of nucleic acids in the subset in which the designated position is occupied by a variant nucleotide and presence of a variant nucleotide at each designated position is called when the number of sequenced nucleic acid in the subset with the variation meets a threshold except as specified in steps (f)(i) and (ii), wherein at least one variant nucleotide which would otherwise have been called in step (d) is not called due to conditions (i) and (ii) being determined to have been met.

28. A method for identifying false positive variant nucleotides in a population of cell-free nucleic acids comprising:
(a) contacting a population of cell-free nucleic acids at least one of which is a double-stranded molecule with single-stranded overhangs at one or both ends and overlapping sequences with a protein having 5'-3' polymerase activity and a 3'-5' exonuclease activity, wherein the protein digests 3' overhangs and fills in 5' overhangs with complementary nucleic acids to generate double-stranded blunt-ended nucleic acids at one or both ends;
(b) determining sequences of a plurality of the double-stranded blunt-ended nucleic acids to provide sequenced nucleic acids;
(c) for each designated position in a reference sequence, identifying a subset of sequenced nucleic acids including the designated position and identifying sequenced nucleic acids in the subset in which the designated position is occupied by a reference nucleotide and the number of sequenced nucleic acids in the subset in which the designated position is occupied by a variant nucleotide; and
(d) calling presence of a false positive variant nucleotide at each designated position at which the sequenced nucleic acids with a C to T or G to A variation at the designated position support the call and the variation is classified as a deamination error based on:
　(1) nucleotide context around the designated position and/or
　(2) overrepresentation of the C to T conversion in sequenced nucleic acids within a first fraction of the subset in which the designated position is within a defined proximity of the 5' end or overrepresentation of the G to A conversion in sequenced nucleic acids in a second fraction of the subset in which the designated position is within a defined proximity of the 3' end; wherein at least one false positive is called.

29. The method of claim 28, wherein the cell-free nucleic acids are cell-free deoxyribonucleic acids (cfDNA).

* * * * *